United States Patent

Takami et al.

[11] Patent Number: 5,935,400
[45] Date of Patent: Aug. 10, 1999

[54] OXYGEN CONCENTRATION DETECTION WITH SENSOR CURRENT LIMITATION

[75] Inventors: Masayuki Takami, Kariya; Tomomichi Mizoguchi, Nagoya; Satoshi Haseda, Okazaki; Kazuhiro Okazaki, Anjo, all of Japan

[73] Assignee: Denso Corporation, Kariya, Japan

[21] Appl. No.: 08/947,398

[22] Filed: Oct. 8, 1997

[30] Foreign Application Priority Data

Oct. 8, 1996 [JP] Japan .................................. 8-267148

[51] Int. Cl.⁶ ........................................................ G01N 27/26
[52] U.S. Cl. .......................... 204/425; 204/406; 204/427; 204/428; 205/784.5
[58] Field of Search ........................ 204/425, 426, 204/427, 428; 123/693, 694; 205/782, 783.5, 785

[56] References Cited

U.S. PATENT DOCUMENTS

| | | | |
|---|---|---|---|
| 4,665,874 | 5/1987 | Kawanabe et al. | 123/440 |
| 4,702,816 | 10/1987 | Hashimoto et al. | 204/406 |
| 4,818,362 | 4/1989 | Asakura et al. | 204/406 |
| 4,908,575 | 3/1990 | Usami et al. | |

FOREIGN PATENT DOCUMENTS

| | | |
|---|---|---|
| A-61-237047 | 10/1986 | Japan . |
| A-61-296260 | 12/1986 | Japan . |
| A-62-280560 | 12/1986 | Japan . |
| A-2-27255 | 1/1990 | Japan . |

*Primary Examiner*—Robert Warden
*Assistant Examiner*—Kaj K. Olsen
*Attorney, Agent, or Firm*—Nixon & Vanderhye P.C.

[57] ABSTRACT

An A/F sensor is driven by a voltage applied thereto at a command issued by a microprocessor, outputting an A/F detection signal which is linearly proportional to the concentration of oxygen. The microprocessor controls the voltage applied to the A/F sensor to bring a current flowing through the A/F sensor to a predetermined value in a zone outside a predetermined air-fuel ratio detection zone. In this outside zone, the applied voltage is controlled in accordance with a characteristic different from a positive characteristic in a normal positive characteristic in a voltage-current relation. That is, in a rich zone outside the air-fuel ratio detection zone, the applied voltage is controlled so as to make the applied voltage approach a maximum value of the electromotive force of the A/F sensor. In a lean zone outside the air-fuel ratio detection zone, on the other hand, the applied voltage is controlled so as to make the applied voltage approach a minimum value of the electromotive force of the A/F sensor.

15 Claims, 14 Drawing Sheets

OXYGEN CONCENTRATION DETECTION WITH SENSOR CURRENT LIMITATION

CROSS REFERENCE TO RELATED APPLICATION

This application is related to and incorporates herein by reference Japanese Patent Application No. 8-267148 filed on Oct. 8, 1996.

BACKGROUND OF THE INVENTION

1. Field of the Invention

The present invention relates to an oxygen-concentration detecting apparatus and method using an oxygen sensor which is used for generating a current signal representing the concentration of oxygen in gas whose oxygen-concentration is to be measured when a voltage is applied to the oxygen sensor. The oxygen-concentration detecting apparatus typically serves as an air-fuel ratio detecting apparatus used in implementation of air-fuel ratio feedback control of an engine employed in a vehicle.

2. Description of Related Art

In recent years, there are a demand for an improved control accuracy and a demand for a transition to lean air-fuel mixture combustion in air-fuel ratio feedback control of an engine employed in a vehicle. In order to respond to these demands, a linear air-fuel ratio sensor (an oxygen sensor) for detecting the air-fuel ratio of mixed air supplied to the engine (oxygen-concentration in exhausted gas) linearly over a wide zone as well as an air-fuel ratio detecting apparatus (an oxygen-concentration detecting apparatus) are implemented into products. In an air-fuel ratio sensor of a limit-current type, a typical air-fuel ratio sensor, a zone for detecting a limit-current is shifted in accordance with the air-fuel ratio (the oxygen-concentration) as is generally known. In detail, as shown in a V-I (voltage-current) characteristic diagram of FIG. 21, the zone for detecting a limit-current comprises straight line segments parallel to a V axis. As shown in the figure, the farther the air-fuel ratio moves to the lean zone, the more the zone for detecting a limit-current is shifted to the positive-voltage side. On the other hand, the farther the air-fuel ratio moves to the rich side, the more the zone for detecting a limit-current is shifted to the negative-voltage side. As a result, if the applied voltage is firmly set at a fixed value at the time the air-fuel ratio changes, it would be impossible to detect an air-fuel ratio with a high degree of accuracy by using the zone for detecting a limit-current (the zone comprising straight line segments parallel to the V axis).

In order to solve this problem, in a conventional ordinary air-fuel ratio detecting apparatus (oxygen-concentration detecting apparatus), the voltage applied to the air-fuel ratio sensor is varied from time to time in accordance with the air-fuel ratio, that is, in accordance with the sensor-current as is the case with those disclosed in Japanese Patent Laid-open Nos. Sho61-237047 and Sho61-280560. In this case, the applied voltage is controlled according to a characteristic line Lx shown in FIG. 21. By controlling the applied voltage in this way, a desired sensor-current, that is, a limit-current can always be obtained. Thus, the characteristic line Lx is given as a linear straight line of a positive characteristic (a characteristic rising to the right) in the V-I coordinate system.

However, the conventional technology described above raises the following problems. In an ordinary air-fuel ratio detecting apparatus, the air-fuel ratio detection zone is set in a predetermined zone. In the case of the V-I characteristic shown in FIG. 21, the air-fuel ratio detection zone covers the A/F ratio zone 12 to 18. By setting the applied voltage in accordance with the characteristic line Lx in this air-fuel ratio detection zone, the air-fuel ratio can be properly detected. For an air-fuel ratio outside the air-fuel ratio detection zone, however, a high voltage on the positive or negative side is applied, giving rise to a problem that an excessively large sensor-current flows, accompanying the high applied voltage. In such a case, a large current flows into a bias control circuit for generating a voltage to be applied to the air-fuel ratio sensor, raising a problem such as dissipation of heat in the circuit.

In more detail, in the event of a fuel cut-off, that is, when the operation to supply fuel to the engine is halted while the engine is operating, for example, the air-fuel ratio shifts far to the lean zone from the air-fuel ratio detection zone. At that time, if a voltage set in accordance with the characteristic line Lx is applied to the air-fuel ratio sensor, an excessively large sensor-current flows, accompanying the applied voltage. In addition, when the amount of injected fuel is raised in response to an increase in load to a heavy one like during acceleration of the vehicle, the air-fuel ratio shifts far to the rich zone. Also in such a case, there is raised a problem that an excessively large sensor-current flows as well.

SUMMARY OF THE INVENTION

It is therefore an object of the present invention to provide an oxygen-concentration detecting apparatus and method that is capable of solving the problems encountered in the conventional air-fuel sensor apparatus by properly controlling the sensor-current in a zone outside the oxygen-concentration detection zone.

According to a first aspect of the present invention, in a zone outside an oxygen-concentration detection zone set in advance, a voltage applied to an oxygen sensor is controlled so as to limit a current flowing through the oxygen sensor to a predetermined value. Here, the oxygen sensor is used as an air-fuel ratio sensor, more specifically, a limit-current type. When the oxygen-concentration detection zone is set as an air-fuel ratio detection zone, the oxygen-concentration detection zone typically corresponds to an air-fuel ratio detection zone covering values of the air-fuel ratio (A/F) ranging from 12 to 18. On the other hand, a zone with A/F<12 or with A/F>18 corresponds to the zone outside the air-fuel ratio detection zone.

By imposing a limit on the current flowing through the oxygen sensor in the zones outside the oxygen-concentration detection zone, the problem caused by an excessively large current flowing through the oxygen sensor can be solved. As a result, the current flowing through the oxygen sensor can be suppressed properly in the zones outside the oxygen-concentration detection zone, allowing the detection of the current to be implemented with a high degree of accuracy. In addition, it is also possible to substantially reduce the amount of heat dissipated in a bias control circuit.

According to a second aspect of the present invention, in an oxygen-concentration detection zone set in advance, a voltage applied to an oxygen sensor is controlled in dependence on a current flowing through the oxygen sensor according to a predetermined positive characteristic on a voltage-current coordinate system and, in a zone outside the oxygen-concentration detection zone, on the other hand, the voltage applied to the oxygen sensor is controlled in accordance with a characteristic different from the positive characteristic. That is, the oxygen sensor provided by the present invention such as an air-fuel ratio sensor of a limit-current type has a voltage-current characteristic with a positive gradient in the oxygen-concentration detection zone. A voltage-current characteristic having a positive gradient which is also referred to hereafter simply as a positive characteristic represents a relation between the voltage applied to the oxygen sensor and the current flowing through the sensor wherein, as one of the voltage and the current increases, the other also increases as well. In this case, by controlling the voltage applied to the oxygen sensor in a zone outside the oxygen-concentration detection zone in accordance with another characteristic different from the positive characteristic, the current flowing through the oxygen sensor can be suppressed properly in the zone outside the oxygen-concentration detection zone, allowing the detection of the current to be implemented with a high degree of accuracy.

It is desirable to provide oxygen-concentration detecting apparatuses according to the present invention of claims 3 through 5 described below as specific means for implementing the oxygen-concentration detecting apparatus according to the present invention of claim 2.

According to a third aspect of the present invention, in a zone outside an oxygen-concentration detection zone set in advance, a voltage applied to an oxygen sensor is feedback-controlled so as to bring a current flowing through the oxygen sensor to a desired target value. By controlling the current flowing through the oxygen sensor toward the desired target value, the sensor-current will neither increase nor decrease unexpectedly. As a result, the current flowing through the oxygen sensor can be suppressed properly in a zone outside the air-fuel ratio detection zone, allowing the current to be detected with a high degree of accuracy.

BRIEF DESCRIPTION OF THE DRAWINGS

Other objects, features and advantages of the invention will be made more apparent by the following detailed description with reference to the accompanying drawings, in which.

DETAILED DESCRIPTION OF THE PREFERRED EMBODIMENT

Figure 1:
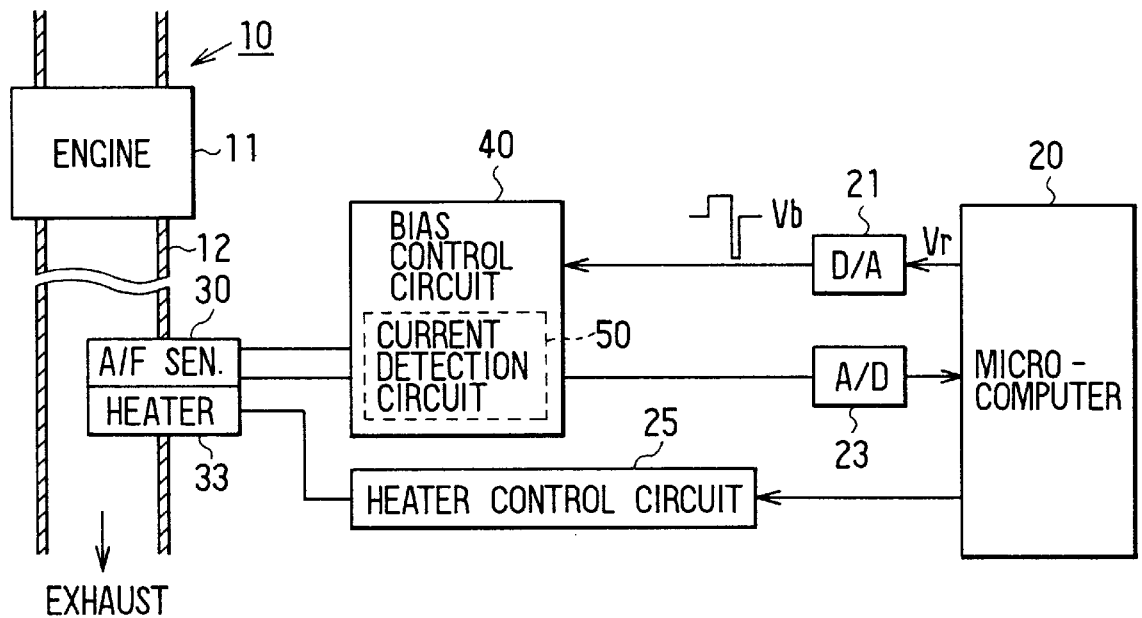
FIG. 1 is a schematic diagram showing the configuration of an air-fuel ratio detecting apparatus implemented by a first embodiment of the present invention.

The present invention will be described in more detail with reference to various embodiments throughout which the same or like parts are designated by the same or like reference numerals.

(First Embodiment)

An air-fuel ratio detecting apparatus implemented by the first embodiment is applied to an electronically-controlled gasoline injection engine mounted on a vehicle. An air-fuel ratio control system of the engine controls the amount of fuel injected to the engine to a desired air-fuel ratio (A/F) on the basis of a result of detection of an air-fuel ratio carried out by the air-fuel ratio detecting apparatus. The following is a detailed description of a procedure for detecting an air-fuel ratio (A/F) by means of an air-fuel ratio sensor of a current limit type used as an oxygen sensor and a procedure for controlling a voltage applied to the sensor.

As shown in FIG. 1, the air-fuel ratio detecting apparatus is provided with an air-fuel ratio detecting sensor 30 of a limit-current type which is referred to hereafter simply as an A/F sensor. The A/F sensor 30 is installed on an exhaust pipe 12 which is extended from the main body 11 of an engine 10. Driven by a voltage applied in accordance with a command issued by a microcomputer 20, the A/F sensor 30 outputs a linear air-fuel ratio detection signal (sensor-current signal) proportional to the concentration of oxygen in the exhaust gas. With components such as a generally known CPU for executing various kinds of processing, a ROM unit and a RAM unit, the microcomputer 20 controls a bias control circuit 40 and a heater control circuit 25 to be described later in accordance with predetermined control programs.

Figure 2:
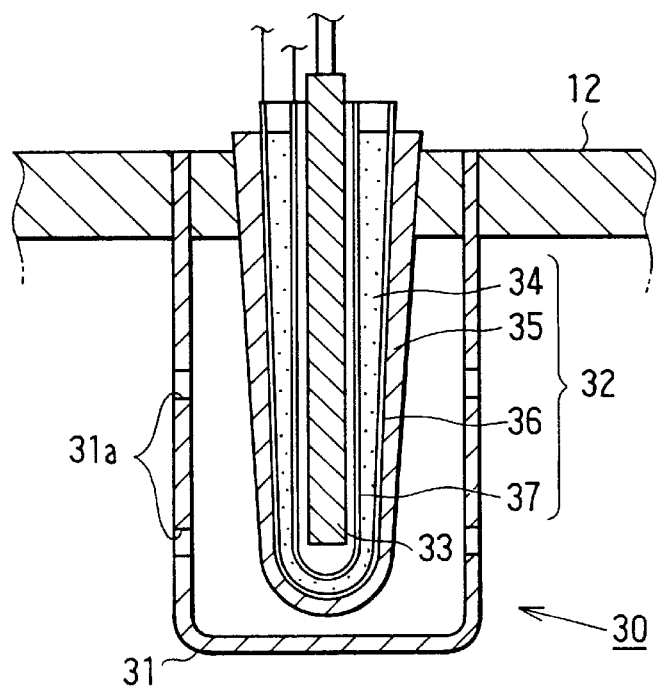
FIG. 2 is a schematic diagram showing a cross section of an A/F sensor.

As shown in FIG. 2, the A/F sensor 30 is provided on the exhaust pipe 12, protruding toward the inside of the exhaust pipe 12. Major components of the A/F sensor 30 are a cover 31, a sensor body 32 and a heater 33. The cross section of the cover 31 has a shape resembling the U-character. A plurality of small holes 31a are bored through the wall of the cover 31 to provide paths from the inside to the outside of the cover 31. The sensor body 32 generates a limit-current representing the oxygen-concentration in a lean zone of the air-fuel ratio or representing the concentration of unburned gas (such as CO, HC and $H_2$) in the rich zone of the air-fuel ratio.

The sensor body 32 comprises a solid electrolyte layer 34 having a cross section with a shape resembling a cup, an exhaust-side electrode layer 36 firmly attached to the external surface of a solid electrolyte layer 34 and an atmosphere-side electrode layer 37 firmly attached to the internal surface of the solid-state electrolyte layer 34. On the outer side of the exhaust-side electrode layer 36, a diffusing resistance layer 35 is provided by adopting typically a plasma spraying method. The solid electrolyte layer 34 is made of an oxygen ion conducting oxide sintered body which is solid-solved in a material such as $ZrO_2$, $HfO_2$, $ThO_2$ and $Bi_2O_3$ with a material such as CaO, MgO, $Y_2O_3$ and $Yb_2O_3$ used as a stabilizer. On the other hand, the diffusing resistance layer 35 is made of a heat resisting inorganic material such as almina, magnesia, silica, spinel and mullite. The exhaust-side electrode layer 36 and the atmosphere-side electrode layer 37 are both made of a noble metal with a high catalytic activity such as platinum and provided by using a porous chemical plating technique. It should be noted that the area and the thickness of the exhaust-side electrode layer 36 is in the zones 10 to 100 square millimeters and 0.5 to 2.0 microns respectively. On the other hand, the area and the thickness of the atmosphere-side electrode layer 37 is in the zones greater than about 10 square millimeters and 0.5 to 2.0 microns respectively.

The heater 33 is accommodated in the atmosphere-side electrode layer 37. The thermal energy generated by the heater 33 heats the sensor body 32 which comprises the atmosphere-side electrode layer 37, the solid-state electrolyte layer 34, the exhaust-side electrode layer 36 and the diffusing resistance layer 35 as described above. The heater 33 has a sufficient capacity of generating heat for activating the sensor body 32.

The A/F sensor 30 having the configuration described above generates a limit-current representing the concentration of oxygen in a zone leaner than the stoichiometric air-fuel ratio point. In this case, the limit-current corresponding to the concentration of oxygen is determined by the area of the exhaust-side electrode layer 36 as well as the thickness, the porosity and the average pore diameter of the diffusing resistance layer 35. The sensor body 32 is capable of detecting the concentration of oxygen in accordance with a linear characteristic thereof. Since a high temperature equal to or higher than about 600 degrees Celsius is required for activating the sensor body 32 and the activating temperature zone is narrow, however, the sensor body 32 can not be controlled in the active zone resulting from heating by only exhaust gas of the engine 10. For this reason, in the present embodiment, the heater 33 is thermally heated by the heater 33 to an activation temperature zone. It should be noted that, in a zone richer than the stoichiometric air-fuel ratio point, the concentrations of unburned gases such as carbon monoxide (CO) change all but linearly with the air-fuel ratio and the sensor body 32 generates a limit-current representing the concentrations of unburned gases such as carbon monoxide (CO).

Figure 3:
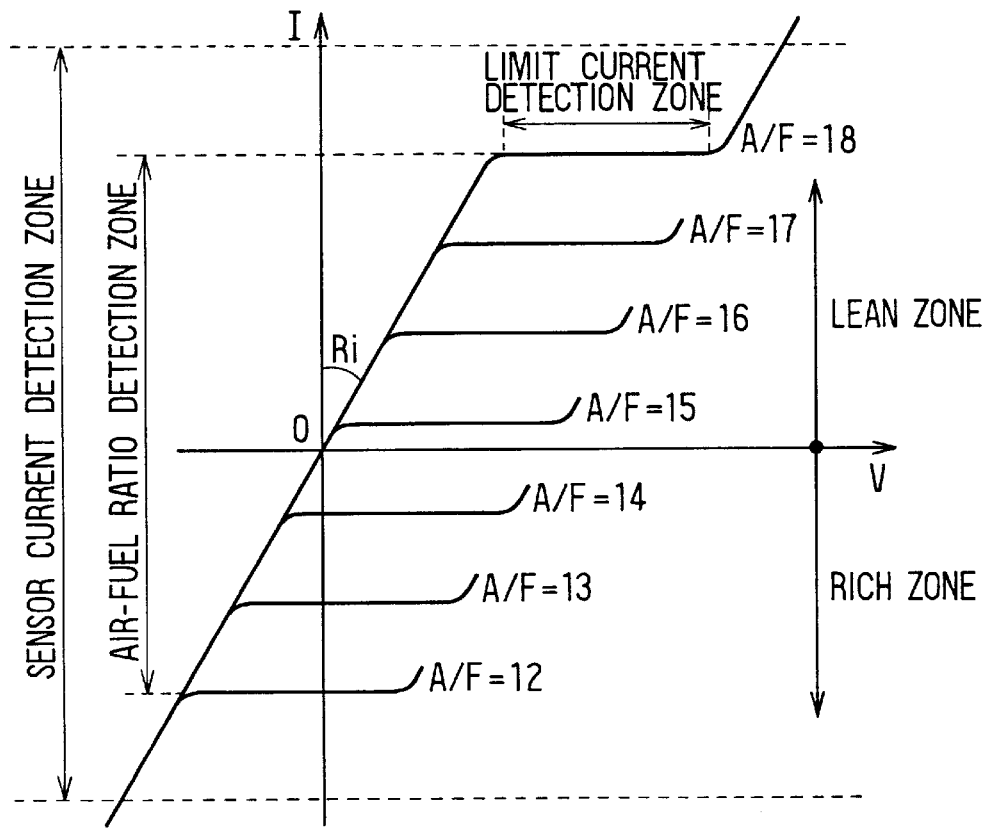
FIG. 3 is a diagram showing a V-I characteristic used for explaining the output characteristic of the A/F sensor.

The voltage-current (V-I) characteristic of the sensor body 32 has, as obvious from FIG. 3, a linear relation between a current flowing to the solid electrolyte layer 34 of the sensor body 32, which is proportional to the A/F detected by the A/F sensor 30, and a voltage applied to the solid electrolyte layer 34. In this case, straight line segments parallel to the voltage axis V each constitute a limit-current detection zone which identifies the limit-current of the sensor body 32. Increases and decreases in limit-current correspond to increases and decreases in air-fuel ratio (that is, shifts to the lean and rich zones). The more the air-fuel ratio is shifted to the lean side, the higher the limit-current becomes. On the other hand, the more the air-fuel ratio is shifted to the rich side, the lower the limit-current becomes.

In addition, in the V-I characteristic, a voltage zone below the straight line segment parallel to the voltage axis V serving as a limit-current detection zone as described above is a resistance dominated zone. The gradient of the linear straight line segment in the resistance dominated zone is determined by the internal resistance of the solid electrolyte layer 34 of the sensor body 32 which is referred to as an element resistance Ri. The element resistance Ri of the solid electrolyte layer 34 of the sensor body 32 changes with temperature. To be more specific, when the temperature decreases, the element resistance Ri of the state electrolyte layer 34 of the sensor body 32 increases, reducing the gradient.

In the characteristic shown in FIG. 3, an air-fuel ratio detection zone is set. In the present embodiment, the zone covers values of the A/F ranging from 12 to 18. In this air-fuel ratio detection zone, air-fuel ratio detection with a high degree of accuracy is assured. The lower and upper limits of the air-fuel ratio detection zone are rich and lean-side limits which correspond to A/Fs of 12 and 18 respectively. By further extending the air-fuel ratio detection zone on the rich and lean sides, a predetermined sensor-current detection zone can be set. Extensions of 20% of the air-fuel ratio detection zone on the rich and lean sides are considered to be appropriate to set the sensor-current detection zone. The setting of the limit-current detection zone is based on a design concept of the bias control circuit 40 shown in FIG. 1. It should be noted that, in order to improve the detection accuracy of the sensor-current, it is desirable to set a sensor-current detection zone which is as narrow as possible.

Figure 4:
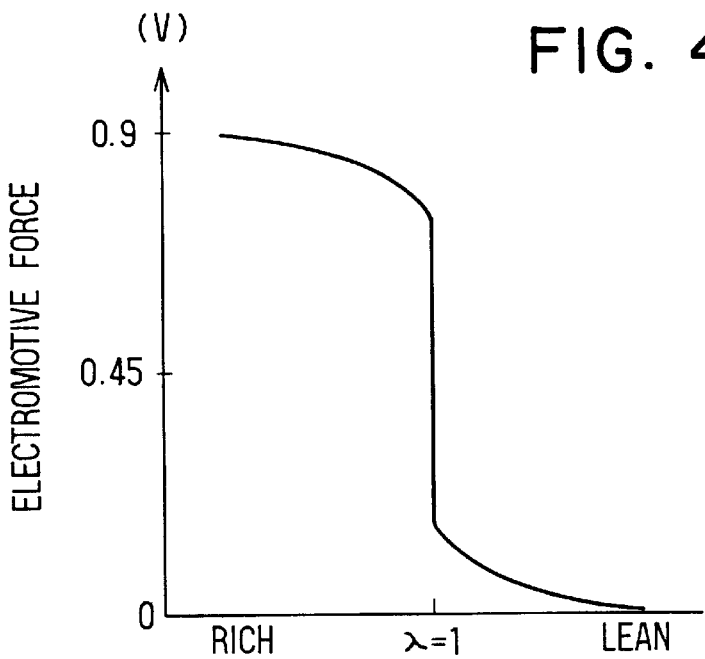
FIG. 4 is a diagram showing an electromotive-force characteristic of the A/F sensor.

As described above, the A/F sensor 30 employed in the present embodiment has an electromotive-force characteristic like one shown in FIG. 4. With no voltage applied to the A/F sensor 30, the electromotive-force characteristic shows an abrupt change in electromotive force when the air-fuel ratio changes from a lean zone to a rich zone across the stoichiometric air-fuel ratio point (LAMBDA=1), the boundary between the lean zone and the rich zone, or vice versa due to a difference in oxygen-concentration between the inside and outside of the solid electrolyte layer 34 of the A/F sensor 30 as shown in the figure. In the electromotive-force characteristic like one shown in FIG. 4, the-electromotive forces are about 0.9 V and 0 V on the rich and lean sides respectively.

In the air-fuel ratio detecting apparatus shown in FIG. 1, the microcomputer 20 outputs a bias command signal Vr, a digital signal for applying a voltage to the A/F sensor 30, to a D/A converter 21 for converting the signal Vr into an analog signal Vb. The analog signal Vb is then supplied to the bias control circuit 40 for generating a voltage for A/F detection to be applied to the A/F sensor 30.

In the A/F detection, different applied-voltage characteristics are used in dependence upon whether the value that the air-fuel ratio has at that time, that is, magnitude of the sensor-current, is in the air-fuel ratio detection zone, in a zone richer than the air-fuel ratio detection zone or in a zone leaner than the air-fuel ratio detection zone. Therefore, applied-voltage control is executed to generate a desired voltage to be applied to the A/F sensor 30. Details of the applied-voltage control will be described in detail later.

The bias control circuit 40 has a current detecting circuit 50 for measuring the value of a current which flows accompanying the application of a voltage to the A/F sensor 30. An analog signal representing the value of the current detected by the current detecting circuit 50 is supplied to the microcomputer 20 through an A/D converter 23. The operation of the heater 33 attached to the A/F sensor 30 is controlled by the heater control circuit 25. In detail, the heater control circuit 25 carries out heating control of the heater 33 by controlling the duty cycle of power supplied to the heater 33 by a battery power supply not shown in the figure in accordance with the element temperature of the A/F sensor 30 and the temperature of the heater 33.

Figure 5:
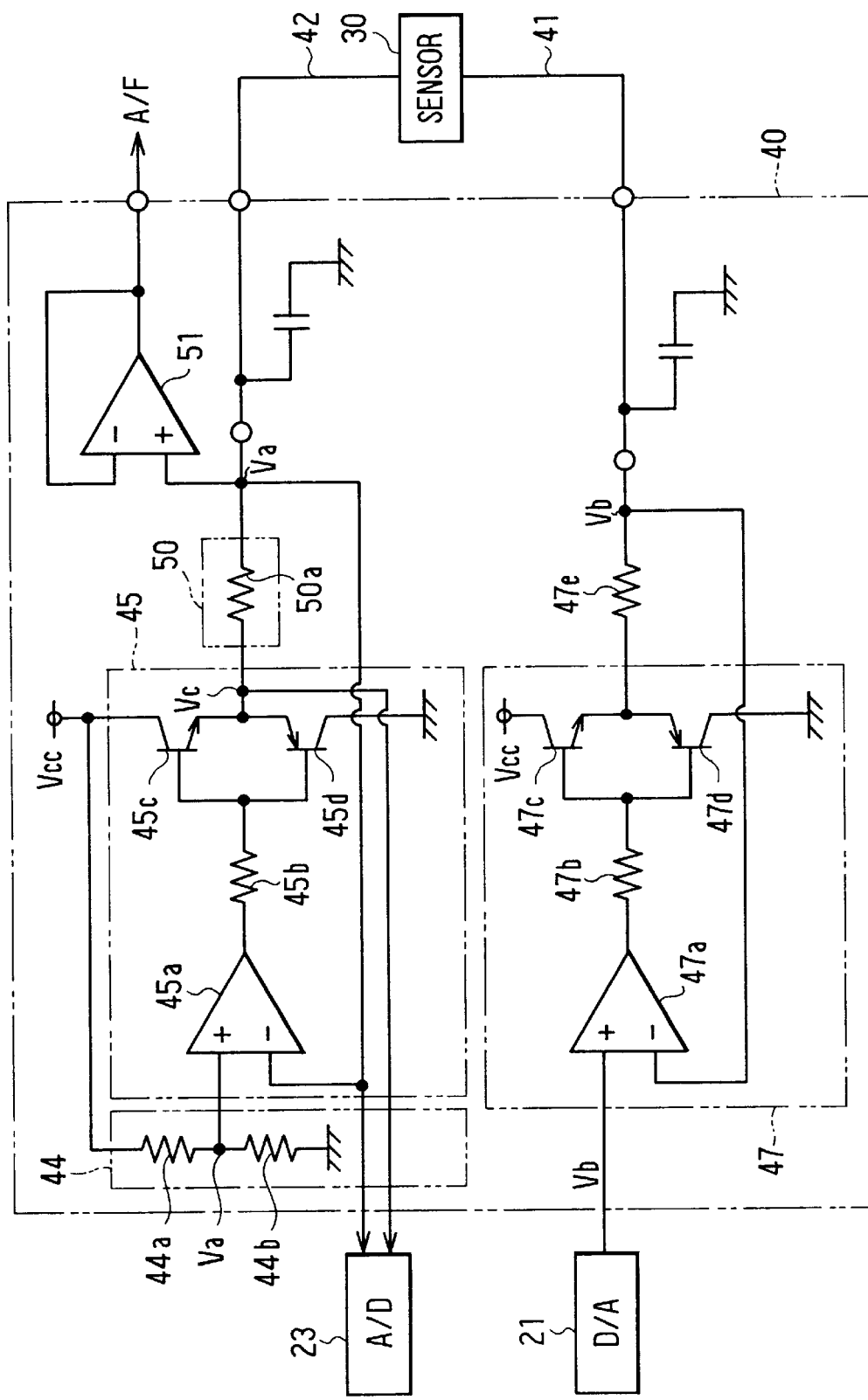
FIG. 5 is an electrical-circuit diagram showing the configuration of a bias control circuit.

As shown in FIG. 5, the bias control circuit 40 comprises major components such as a reference voltage circuit 44, a first voltage supplying circuit 45, a second voltage supplying circuit 47 and the current detecting circuit 50. The reference voltage circuit 44 generates a fixed reference voltage Va by dividing a constant voltage Vcc by means of a potentiometer comprising resistors 44a and 44b.

Implemented as a voltage follower circuit, the first voltage supplying circuit 45 supplies a voltage Va equal in level to the reference voltage Va generated by the reference voltage circuit 44 to a terminal 42 of the A/F sensor 30. It should be noted that the terminal 42 is connected to the atmosphere-side electrode layer 37 shown in FIG. 2. In more detail, the first voltage supplying circuit 45 comprises an operational amplifier 45a, a resistor 45b, an NPN transistor 45c and a PNP transistor 45d. The positive input terminal of the operational amplifier 45a is connected to the junction between the resistors 44a and 44b of the potentiometer employed in the reference voltage generator 44. The negative input terminal and the output terminal of the operational amplifier 45a are connected to the terminal 42 of the A/F sensor 30 and one end of the resistor 45b respectively. The other end of the resistor 45b is connected to the junction between the bases of the NPN transistor 45c and the PNP transistor 45d. The collector and emitter of the NPN transistor 45c are connected to the constant voltage Vcc and the emitter of the PNP transistor 45d respectively. The junction between the emitters of the NPN transistor 45c and the PNP transistor 45d is connected to the terminal 42 of the A/F sensor 30 through a current detecting resistor 50a which serves as the current detecting circuit 50. The collector of the PNP transistor 45d is connected to the ground.

Much like the first voltage supplying circuit 45, the second voltage supplying circuit 47 is implemented as a voltage follower circuit, supplying a voltage Vb equal in level to a voltage Vb generated by the D/A converter 21 to the other terminal 41 of the A/F sensor 30. It should be noted that the terminal 41 is connected to the exhaust-side electrode layer 36 shown in FIG. 2. In more detail, the first voltage supplying circuit 47 comprises an operational amplifier 47a, a resistor 47b, an NPN transistor 47c and a PNP transistor 47d. The positive input terminal of the operational amplifier 47a is connected to the output terminal of the D/A converter 21. The negative input terminal and the output terminal of the operational amplifier 47a are connected to the other terminal 41 of the A/F sensor 30 and one end of the resistor 47b respectively. The other end of the resistor 47b is connected to the junction between the bases of the NPN transistor 47c and the PNP transistor 47d. The collector and emitter of the NPN transistor 47c are connected to the constant voltage Vcc and the emitter of the PNP transistor 47d respectively. The junction between the emitters of the NPN transistor 47c and the PNP transistor 47d is connected to the other terminal 41 of the A/F sensor 30 through a resistor 47e. The collector of the PNP transistor 47d is connected to the ground.

With the configuration described above, the reference voltage Va is supplied to the terminal 42 of the A/F sensor 30 all the time. On the other hand, the voltage Vb is supplied to the other terminal 41 of the A/F sensor 30 by the D/A converter 21. If the voltage Vb is lower than the reference voltage Va (Vb<Va), a positive bias is applied to the A/F sensor 30. If the voltage Vb applied to the other terminal 41 of the A/F sensor 30 is higher than the reference voltage Va (Vb>Va), on the other hand, a negative bias is applied to the A/F sensor 30. In either case, a sensor-current (a limit-current) which flows accompanying the applied voltage is detected as a difference (Vc-Va) in electric potential between the ends of the current detecting resistor 50a. The difference in electric potential is supplied to the microcomputer 20 by way of the A/D converter 23.

In addition, an output buffer 51 is connected between the terminal 42 of the A/F sensor 30 and the current detecting circuit 50. The output buffer 51 is used for directly fetching the detected air-fuel ratio as a voltage signal.

It should be noted that, as described earlier, the air-fuel ratio detecting apparatus is applied to a control system of a vehicle which is neither shown in the figure nor described in detail. The control system is provided with a microcomputer for the commonly known engine control. To be more specific, the microcomputer is used for carrying out feedback control of the air-fuel ratio based on a result of detection performed by the A/F sensor 30. The control carried out by the microcomputer is carried out to adjust the amount of fuel supplied by injection from an injector to cylinders.

Next, a function specific to the present embodiment is explained. The present embodiment is constructed to limit the sensor-current for zones outside the air-fuel ratio detection zone shown in FIG. 3 to values in a predetermined zone. The outline of this function is described by referring to the V-I characteristic diagram shown in FIG. 7.

Figure 7:
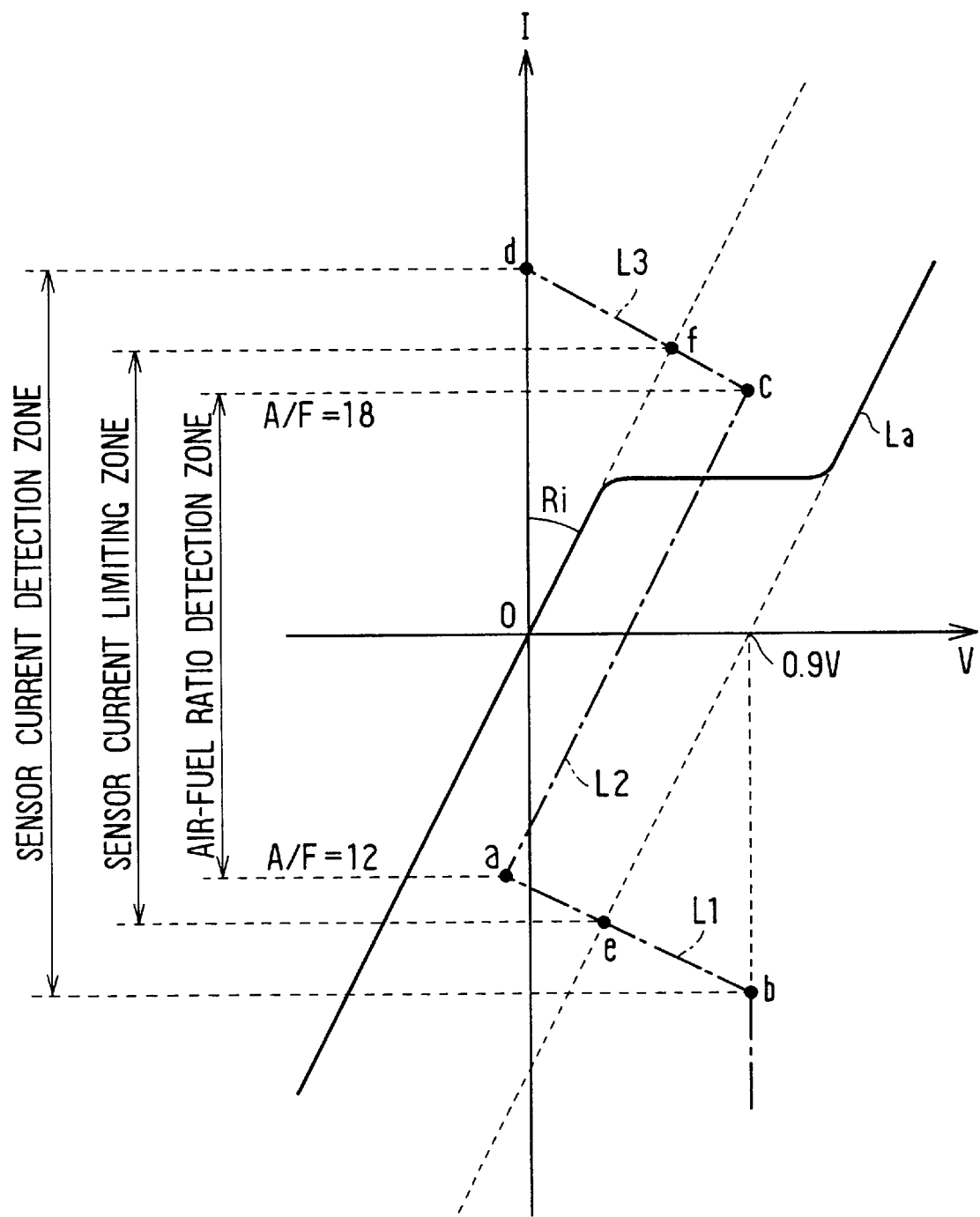
FIG. 7 is a diagram showing a V-I characteristic used for explaining the applied-voltage characteristic of the A/F sensor.

As shown in FIG. 7, in the air-fuel ratio detection zone where A/F=12 to 18, a normal characteristic line L2 is set. The characteristic line L2 is used for controlling the applied voltage. The characteristic line L2 is given as a linear straight line having about the same gradient as the V-I characteristic line, a characteristic line La shown by a solid line in the figure. As described earlier, the gradient of the V-I characteristic line is determined by the element resistance Ri of the A/F sensor 30. That is, the characteristic line L2 exhibits a positive characteristic representing a relation between the applied voltage and the sensor-current wherein, as one of the voltage and the sensor-current increases, the other also increases as well.

In addition, on the side richer than the air-fuel ratio detection zone where A/F<12, a characteristic line L1 having a gradient opposite to the positive gradient of the characteristic line L2, that is, having a negative gradient, is set. A point a is a limit point of the characteristic line L2 on the rich side of the air-fuel ratio detection zone. On the other hand, a point b is a point of intersection of a limit line of the sensor-current detection zone on the rich side and a line representing an electromotive force of 0.9 V of the A/F sensor 30 on the rich side. The characteristic line L1 includes a linear straight line segment connecting the points a and b.

It should be noted that a portion of the characteristic line L1 on the side richer than the sensor-current detection zone is a straight line segment parallel to the I axis representing the 0.9 V electromotive force.

In addition, on the side leaner than the air-fuel ratio detection zone where A/F>18, a characteristic line L3 also having a gradient opposite to the positive gradient of the characteristic line L2, that is, having a negative gradient, is set. A point c is a limit point of the characteristic line L2 on the lean side of the air-fuel ratio detection zone. On the other hand, a point d is a point of intersection of a limit line of the sensor-current detection zone on the lean side and a line representing an electromotive force of 0 V of the A/F sensor 30 on the lean side. The characteristic line L3 includes a linear straight line segment connecting the points c and d. It should be noted that a portion of the characteristic line L3 on the side leaner than the sensor-current detection zone is a straight line segment parallel to the I axis representing the 0V electromotive force.

By setting the characteristic lines L1 and L3 as described above, in a state shown in FIG. 7, that is in a state wherein the element resistance has a predetermined value Ri, it is a matter of course that, for a zone outside the air-fuel ratio detection zone, the sensor-current flowing at that time is limited to values in the sensor-current detection zone.

Figure 8A:
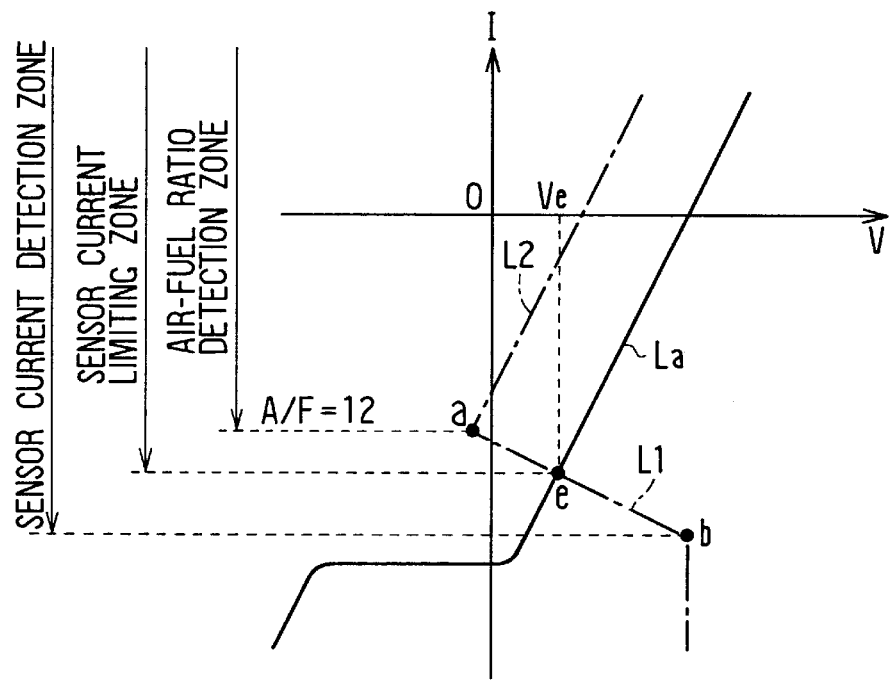
FIGS. 8(a) and 8(b) are diagrams showing V-I characteristics used for explaining the applied-voltage characteristic of the A/F sensor.

As shown in FIG. 8(a), when fuel is more injected so that the air-fuel ratio changes to a richer value on the side richer than the rich-side limit of the air-fuel ratio detection zone representing an A/F of 12, the V-I characteristic line La crosses the characteristic line L1 at a point e. This means that, if the air-fuel ratio changes from 12 to a value on the side richer than the rich-side limit of the air-fuel ratio detection zone representing an A/F of 12, the applied voltage gradually changes along the characteristic line L1 from the point a to the point e representing a voltage Ve, staying at the point e. That is, even if the air-fuel ratio further changes to a value much richer than the point e, the sensor-current is limited by a lower current limit corresponding to the point e because the applied voltage is fixed at the voltage Ve.

Figure 8B:
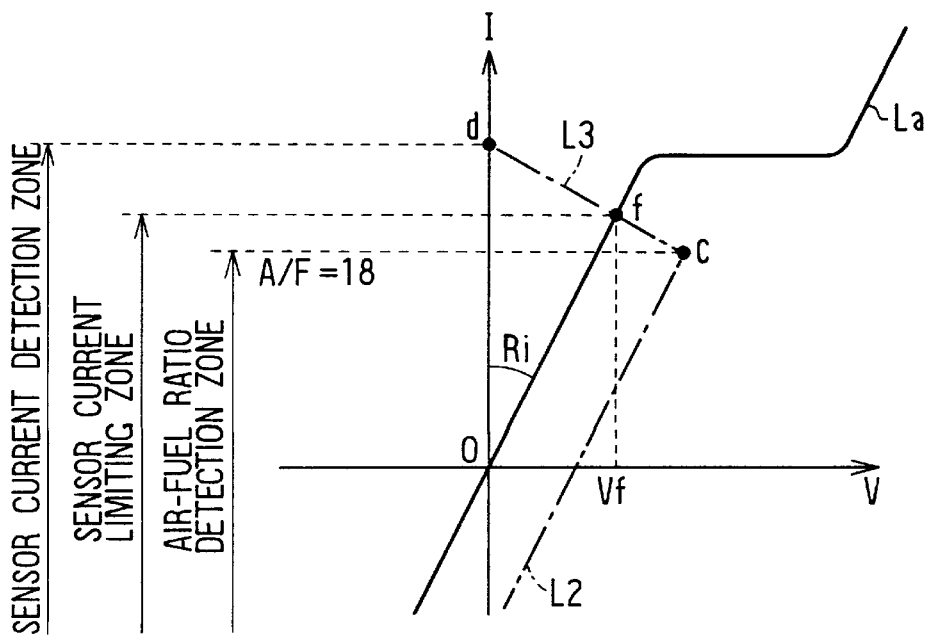

When fuel is less injected so that the air-fuel ratio changes to a leaner value on the side leaner than the lean-side limit of the air-fuel ratio detection zone representing an A/F of 18, on the contrary, the V-I characteristic line La crosses the characteristic line L3 at a point f as shown in FIG. 8(b). This means that, if the air-fuel ratio changes from 18 to a value on the side leaner than the lean-side limit of the air-fuel ratio detection zone representing an A/F of 18, the applied voltage gradually changes along the characteristic line L3 from the point c to the point f representing a voltage Vf, staying at the point f. That is, even if the air-fuel ratio further changes to a value much leaner than the point f, the sensor-current is limited by an upper current limit corresponding to the point f because the applied voltage is fixed at the voltage Vf.

Thus, it is possible to set a sensor-current limitation zone which goes beyond the air-fuel ratio detection zone but remains within the sensor-current detection zone in the V-I characteristic diagram of FIG. 7. By setting such a sensor-current limitation zone, the value of the current flowing through the A/F sensor 30 will never goes beyond the sensor-current limitation zone, a current zone prescribed by the points e and f.

Figure 9:
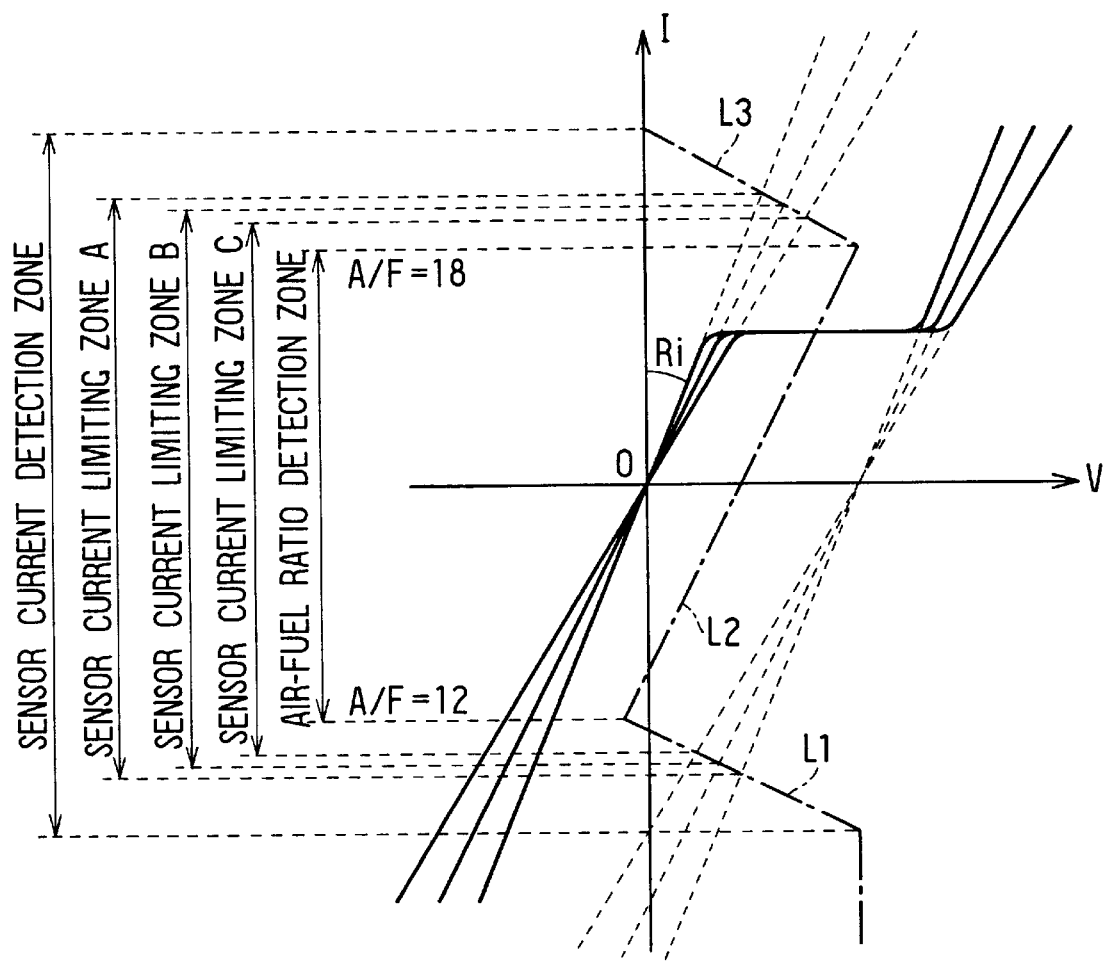
FIG. 9 is a diagram showing a V-I characteristic used for explaining the applied-voltage characteristic of the A/F sensor.

Here, the value of the element resistance Ri shown in FIG. 7 changes in accordance with the activation state of the A/F sensor 30. Thus, the gradient of the V-I characteristic line La also changes in accordance with the activation state of the A/F sensor 30. It should be noted that FIG. 9 shows states in which, the smaller the element resistance Ri, the more the A/F sensor 30 is activated. As is obvious from the figure, when the state of activation of the A/F sensor 30 changes, the sensor-current limitation zone also changes as indicated by symbols A, B and C in the figure. In either case, however, the sensor-current is limited by the respective sensor-current limitation zone A, B or C, hence, never going beyond the sensor-current detection zone. As a result, the problem caused by an excessively flowing sensor-current is solved.

The first embodiment operates as follows based on the processing shown in FIG. 6 which is started by the microcomputer 20 at the time the power supply is turned on.

As shown in the figure, the flow of processing begins with a step 100 at which the microcomputer 20 makes a determination as to whether or not a predetermined time T1 has lapsed since the immediately previous detection of the sensor-current. The predetermined time T1 is a period of detection of the sensor-current Ip. It is proper to set the time T1 typically at a value in the zone 2 to 4 ms (milliseconds). If the predetermined time T1 has lapsed since the immediately previous detection of the sensor-current Ip, that is, if the result of the determination made by the microcomputer 20 at the step 100 is YES, the flow of processing goes on to a step 110.

At the step 110, the microcomputer 20 inputs the sensor-current (the limit-current) Ip detected by the current detecting circuit 50 and reads out an A/F of the engine corresponding to the sensor-current Ip from a map stored in advance in the ROM unit of the microcomputer 20. It should be noted, however, that the sensor-current Ip does not have to be converted into an A/F. Instead, the detected value of the sensor Ip can be used as it is as shown in the figure.

Then, at steps 120 to 160, the microcomputer 20 determines the value of a voltage to be applied to the A/F sensor 30 from the detected value of the sensor-current. In detail, at the step 120, the microcomputer 20 makes a determination as to whether or not the sensor-current Ip is equal to or smaller than a rich-side limit of the air-fuel ratio detection zone, that is, whether or not the sensor-current Ip is equal to or smaller than a current value corresponding to an A/F of 12. If the sensor-current Ip is equal to or smaller than the rich-side limit of the air-fuel ratio detection zone, that is, if the result of the determination made by the microprocessor 20 at the step 120 is YES, the flow of processing proceeds to a step 140. If the sensor-current Ip is greater than the rich-side limit, on the other hand, the flow of processing continues to a step 130.

At the step 130, the microcomputer 20 makes a determination as to whether or not the sensor-current Ip is equal to or smaller than a lean-side limit of the air-fuel ratio detection zone, that is, whether or not the sensor-current Ip is equal to or smaller than a current value corresponding to an A/F of 18. If the sensor-current Ip is equal to or smaller than the lean-side limit of the air-fuel ratio detection zone, that is, if the result of the determination made by the microprocessor 20 at the step 130 is YES, the flow of processing proceeds to a step 150. If the sensor-current Ip is greater than the lean-side limit, on the other hand, the flow of processing continues to a step 160.

At the step 140 for which Ip has been found equal to or smaller than the rich-side limit (Ip≦Rich-side limit) at the step 120, the microcomputer 20 computes the value of the voltage Vp to be applied to the A/F sensor 30 for the sensor-current Ip detected at the step 110 by using the characteristic line L1 of FIG. 7 which is stored in advance in the ROM unit. The voltage Vp to be applied to the A/F sensor 30 is a voltage for limiting the sensor-current in a rich zone.

In addition, at the step 150 for which Ip has been found equal to or smaller than the lean-side limit but greater than the rich-side limit (Rich-side limit<Ip≦Lean-side limit) at the step 130, the microcomputer 20 computes the value of the voltage Vp to be applied to the A/F sensor 30 for the sensor-current Ip detected at the step 110 by using the characteristic line L2 of FIG. 7 which is stored in advance in the ROM unit. The voltage Vp to be applied to the A/F sensor 30 is a voltage for use in an operation in a normal state.

Furthermore, at the step 160 for which Ip has been found equal to or greater than the lean-side limit at the step 130, the microcomputer 20 computes the value of the voltage Vp to be applied to the A/F sensor 30 for the sensor-current Ip detected at the step 110 by using the characteristic line L3 of FIG. 7 which is stored in advance in the ROM unit. The voltage Vp to be applied to the A/F sensor 30 is a voltage for limiting the sensor-current in a lean zone.

Thereafter, the flow of processing goes on from the step 140, 150 or 160 to a step 170 at which the microcomputer 20 produces a bias command signal Vr from the applied voltage Vp computed at the step 140, 150 or 160, outputting the bias command signal Vr to the D/A converter 21. In this way, the desired voltage Vp is applied to the A/F sensor 30.

Figure 10:
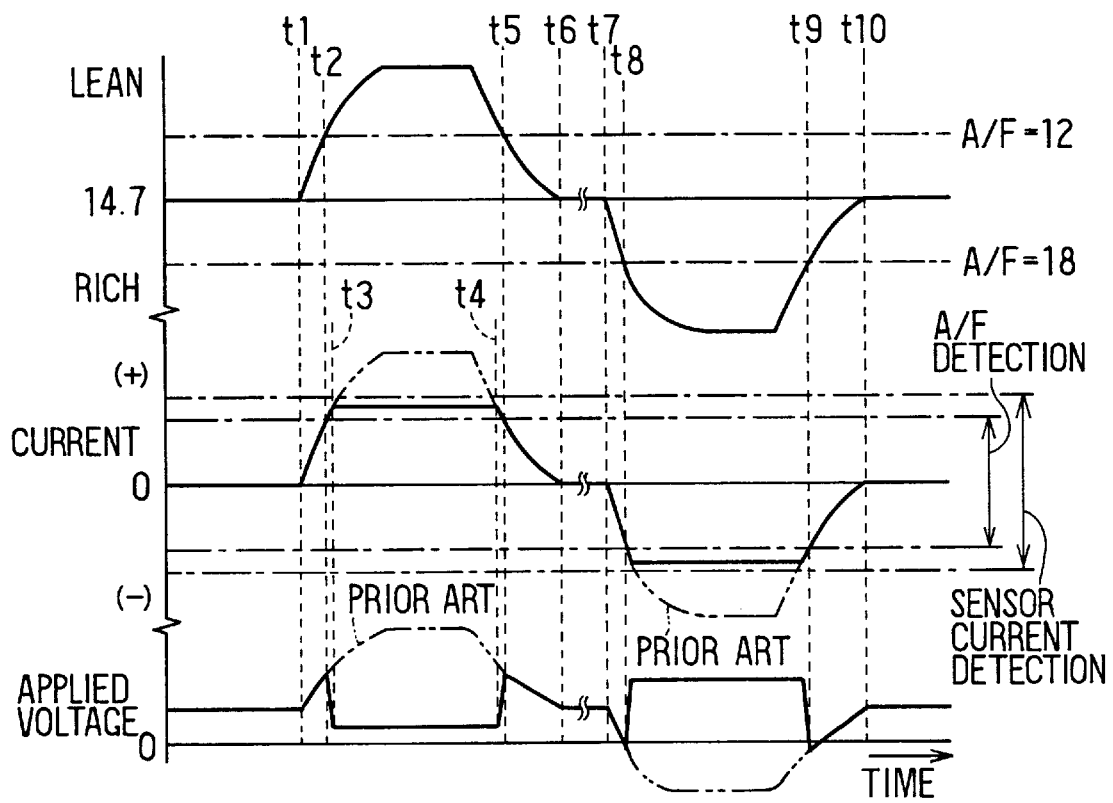
FIG. 10 is a time chart showing the operations of the first embodiment.
Figure 21:
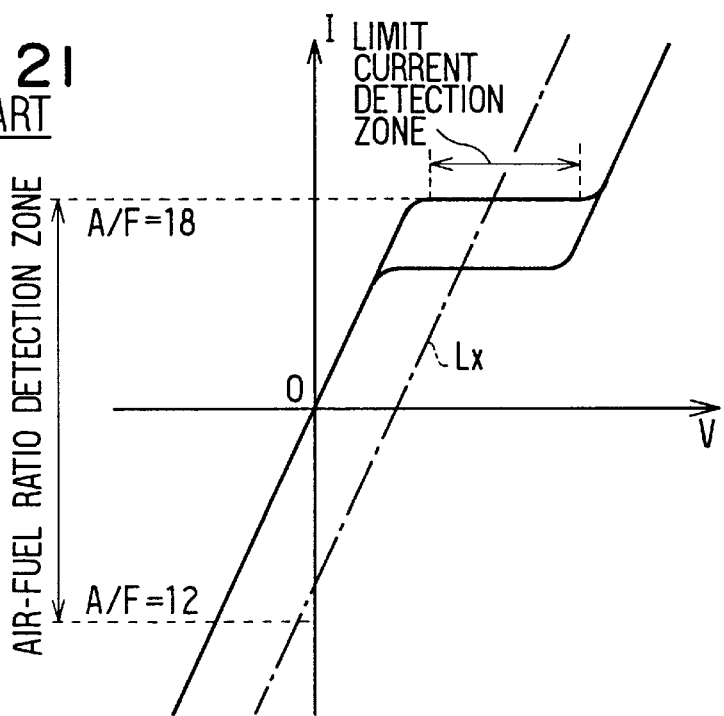
FIG. 21 is a diagram showing a V-I characteristic used for explaining the applied-voltage characteristic of the A/F sensor according to a conventional technology.

In the time chart shown in FIG. 10, air-fuel ratio feedback control is implemented for a stoichiometric air-fuel ratio (A/F) of 14.7 as a background. In a period between points of time t1 and t6, however, the air-fuel ratio shifts far to the lean zone temporarily in the event of a fuel cut-off for example. In a period between points of time t7 and t10, on the other hand, the air-fuel ratio shifts far to the rich zone temporarily in the event of injection of a large amount of fuel in response to an increase in load to a heavy one for example. It should be noted that, in the time chart shown in FIG. 10, solid lines represent the sensor-current and the applied voltage generated in accordance with the control implemented by the present embodiment while double-dotted lines represent the sensor-current and the applied voltage generated in accordance with the conventional control, that is, the control of the applied voltage using the characteristic line Lx shown in FIG. 21.

First of all, prior to the point of time t1, feedback control is implemented with the stoichiometric air-fuel ratio (having a value of 14.7) used as a target air-fuel ratio. In this case, the resulting air-fuel ratio approximately matches the stoichiometric air-fuel ratio. Then, at the point of time t1 where the fuel cut-off is started, the air-fuel ratio changes to a value located far in the lean zone and the sensor-current accordingly changes to a value located far on the positive side.

Later on, at a point of time t2 where the sensor-current reaches a value on the lean-side limit of the air-fuel ratio detection zone corresponding to an A/F of 18 represented by the point c shown in FIG. 7, the applied voltage which has been exhibiting an ascending trend so far turns off to a descending trend. This is because, prior to the point of time t2, the applied voltage is controlled by using the characteristic line L2 shown in FIG. 7 while, after the point of time t2, the control of the applied voltage is based on the characteristic line L3 shown in FIG. 7. In a period between the point of time t2 and a point of time t3, the applied voltage is controlled along the characteristic line L3, approaching 0 V gradually.

Then, at the point of time t3 where the sensor-current reaches a value on the lean-side limit of the sensor-current limitation zone, the sensor-current and the applied voltage remain unchanged from their values at the point of time t3 represented by the point f shown in FIG. 7 even if the air-fuel ratio further changes to a value located farther in the lean zone. It should be noted, however, that a variation in element resistance Ri causes the sensor-current and the applied voltage to change even though the changes in current and voltage are small depending upon the value of the element resistance Ri at that time as shown in FIG. 9. That is, the point f shown in FIG. 7 is shifted to the right or left along the characteristic line L3. Thereafter, the air-fuel ratio once gets in a state close to the atmospheric state but, as the injection of fuel by the injector is resumed with predetermined timing, the air-fuel ratio starts to decrease.

At a point of time t4, the sensor-current starts to decrease to a value smaller than a limit value on the lean side of the sensor-current limitation zone and, accordingly, the applied voltage starts to rise along the characteristic line L3 shown in FIG. 7, making a gradual transition from the point f to the point c shown in the figure. At a point of time t5 where the air-fuel ratio gets in the air-fuel ratio detection zone and the sensor-current becomes smaller than the value corresponding to the lean-side limit, the applied voltage is thereafter controlled by again using the characteristic line L2 shown in FIG. 7. Finally, at the point of time t6, the air-fuel ratio is restored to the stoichiometric air-fuel ratio.

Comparison of the control according to the present embodiment with the conventional control during the period where the air-fuel ratio goes beyond the air-fuel ratio detection zone, getting in the lean zone, that is, during the period between the points of time t2 and t5, indicates that, in the case of the conventional control shown by the double-dotted lines, the applied voltage rises following the change in air-fuel ratio, causing the sensor-current to go far beyond the sensor-current detection zone. In the case of the control implemented by the present embodiment shown by the solid lines, on the other hand, it is obvious that the sensor-current is limited to values in the sensor-current detection zone when the air-fuel ratio changes.

The following is description of a case in which injection of a large amount of fuel in response to an increase in load to a heavy one is started at the point of time t7. In this case, however, since the only difference is the fact that the air-fuel ratio changes to a value in the rich zone, the explanation is focused on essential points only.

First, after the point of time t7 at which the load starts to increase to a high value, the air-fuel ratio greatly changes to a value in the rich zone and the current also changes to a value on the negative side due to the change in air-fuel ratio. Later on, at a point of time t8 where the sensor-current reaches a value on the rich-side limit of the air-fuel ratio detection zone corresponding to an A/F of 12 represented by the point a shown in FIG. 7, the applied voltage which has been exhibiting a descending trend so far turns off to an ascending trend. This is because, prior to the point of time t8, the applied voltage is controlled by using the characteristic line L2 shown in FIG. 7 while, after the point of time t8, the control of the applied voltage is based on the characteristic line L1 shown in FIG. 7. After the point of time t8, the applied voltage is controlled along the characteristic line L1, approaching 0.9 V gradually.

Then, when the sensor-current reaches a value on the rich-side limit of the sensor-current limitation zone, the sensor-current and the applied voltage remain unchanged from predetermined values represented by the point e shown in FIG. 7 even if the air-fuel ratio further changes to a value located farther in the rich zone. Thereafter, when the increase in load to a heavy one disappears and the sensor-current starts to rise due to an increase in air-fuel ratio, the applied voltage starts to decrease along the characteristic line L1 shown in FIG. 7, making a gradual transition from the point e to the point a shown in the figure. At a point of time t9 where the air-fuel ratio gets in the air-fuel ratio detection zone, the applied voltage is thereafter controlled by again using the characteristic line L2 shown in FIG. 7. Finally, at the point of time t10, the air-fuel ratio is restored to the stoichiometric air-fuel ratio.

Comparison of the control according to the present embodiment with the conventional control during the period where the air-fuel ratio goes beyond the air-fuel ratio detection zone, getting in the rich zone, that is, during the period between the points of time t8 and t9, indicates that, in the case of the conventional control shown by the double-dotted lines, the applied voltage decreases following the change in air-fuel ratio, causing the sensor-current to go far beyond the sensor-current detection zone. In the case of the control implemented by the present embodiment shown by the solid lines, on the other hand, it is obvious that the sensor-current is limited to values in the sensor-current detection zone when the air-fuel ratio changes.

Advantages exhibited by the first embodiment are described as follows.

(a) In the present embodiment, in zones outside the air-fuel ratio detection zone, that is, in zones shown in FIG. 7 where A/F<12 and A/F>18, the voltage applied to the A/F sensor 30 is controlled so as to limit the sensor-current to values in a predetermined zone. That is, if normal control of the applied voltage based on the air-fuel ratio is implemented also in zones outside the air-fuel detection zone, there will be raised a problem such as a large current flowing through the A/F sensor 30 as is the case with the conventional technology described earlier. In the case of the present embodiment, on the other hand, by imposing a limit on the sensor-current, the problem caused by an excessively large current flowing through the A/F sensor 30 can be solved. As a result, the sensor-current can be suppressed properly in a zone outside the air-fuel ratio detection zone, allowing the detection of the current to be implemented with a high degree of accuracy. In addition, it is also possible to substantially reduce the amount of heat dissipated in the bias control circuit 40 which is used for applying a voltage to the A/F sensor 30, more specifically, the amount of heat dissipated in driving operations carried out by a transistor employed in the circuit.

(b) More specifically, in the air-fuel ratio detection zone, the applied voltage is controlled in accordance with a predetermined positive characteristic in the V-I coordinate system, that is, the characteristic line L2 shown in FIG. 7. In zones outside the air-fuel ratio detection zone, on the other hand, the applied voltage is controlled in accordance with characteristics different from the positive characteristic in the V-I coordinate system, that is, the characteristic lines L1 and L3 shown in FIG. 7 for the rich and lean zones respectively. As a result, by controlling the applied voltage in accordance with the characteristic lines L1 and L3, the detection of the current can be implemented with a high degree of accuracy.

(c) In particular, the characteristic line L1 shown in FIG. 7 is used for controlling the applied voltage so that the voltage gradually approaches a maximum value of 0.9 V of the electromotive force of the A/F sensor 30 for sensor-currents on the side richer than the air-fuel ratio detection zone while the characteristic line L3 shown in FIG. 7 is used for controlling the applied voltage so that the voltage gradually approaches a minimum value of 0 V of the electromotive force of the A/F sensor for sensor-currents on the side leaner than the air-fuel ratio detection zone. In addition, the characteristic lines L1 and L3 are set so that the sensor-current is limited to values outside the air-fuel ratio detection zone but within the sensor-current detection zone.

With the configuration described above, in the sensor-current limitation zone, a zone between the points e and f shown in FIG. 7, the sensor-current is limited, so that a sensor-current outside the sensor-current limitation zone does not flow. In addition, the sensor-current limitation zone can be contained within the sensor-current detection zone even if the element resistance Ri of the A/F sensor 30 changes as shown in FIG. 9.

(d) In addition, according to the present embodiment, since a sensor-current in the sensor-current detection zone can always be detected even if the air-fuel ratio changes to a value located far in the lean or rich zone, the element resistance Ri of the A/F sensor 30 can be detected at any time.

(e) Furthermore, in the present embodiment, since the sensor-current can be limited as described above, the amount of heat dissipated in the bias control circuit 40 can be suppressed. As a result there is no need for an additional configuration to provide a resistor for limiting the sensor-current in the bias control circuit 40, for example, resistors between the constant voltage Vcc and the transistors 45c and 47c shown in FIG. 5 and, at the same time, the accuracy of the detection of the sensor-current can be assured.

Figure 11:
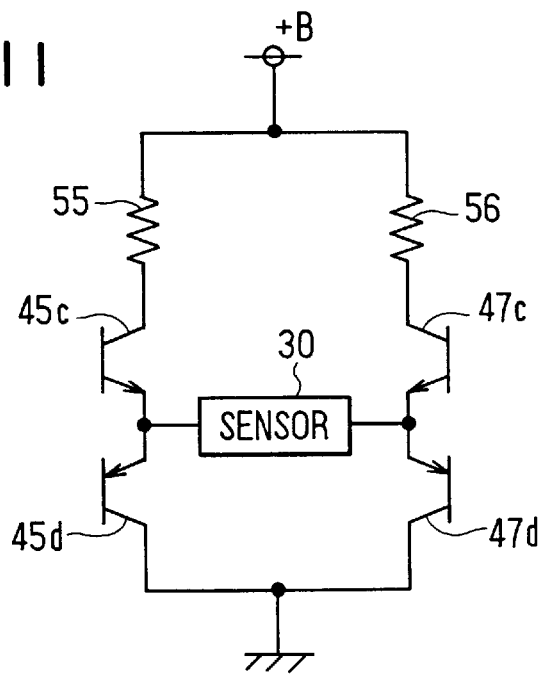
FIG. 11 is diagram showing an equivalent circuit used for explaining advantages exhibited by the first embodiment.

If a battery voltage +B is used in place of the 5 V constant voltage vcc shown in FIG. 5, a capability of detecting the air-fuel ratio over the entire zone of a wide zone must be assured because the voltage +B has a value widely ranging from 8 to 16 V and, in addition, the amount of heat dissipated in the circuit due to a current flowing thereto must be reduced, making a resistor for limiting the magnitude of the current indispensable. Specifically, a resistor 55 for limiting the magnitude of the current would be otherwise connected between the terminal of the battery generating the voltage B+ and the collector of the NPN transistor 45c whereas a current limiting resistor 56 would be likewise connected between the terminal of the battery generating the voltage B+ and the collector of the NPN transistor 47c as shown in an equivalent circuit of FIG. 11. Such current limiting resistors might be hindrances to make the circuit small in size and low in cost. With the configuration provided by the present embodiment, however, the sensor-current can be controlled, allowing the amount of heat dissipated in the circuit to be suppressed without resorting to a current limiting means such as the resistors 55 and 56.

(Second Embodiment)

The second embodiment is characterized in that, in the case of an air-fuel ratio or the sensor-current going beyond the air-fuel ratio detection zone, the sensor-current is feedback-controlled toward a predetermined target value in the sensor-current detection zone. Essentials of the second embodiment are described by referring to FIGS. 12 to 14 as follows.

Figure 6:
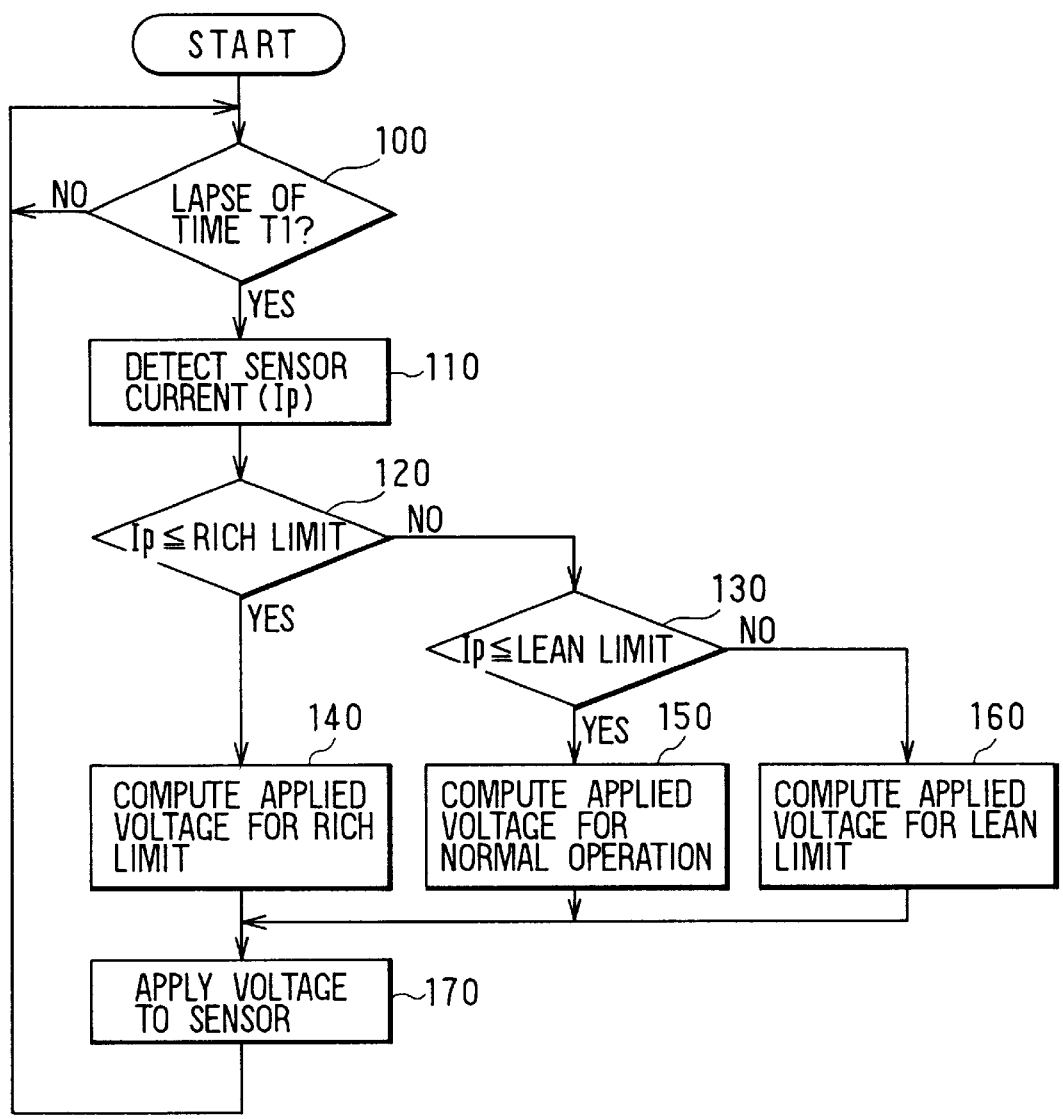
FIG. 6 is a flowchart showing a procedure for detecting a sensor-current and controlling a voltage applied to the A/F sensor according to the first embodiment.
Figure 12:
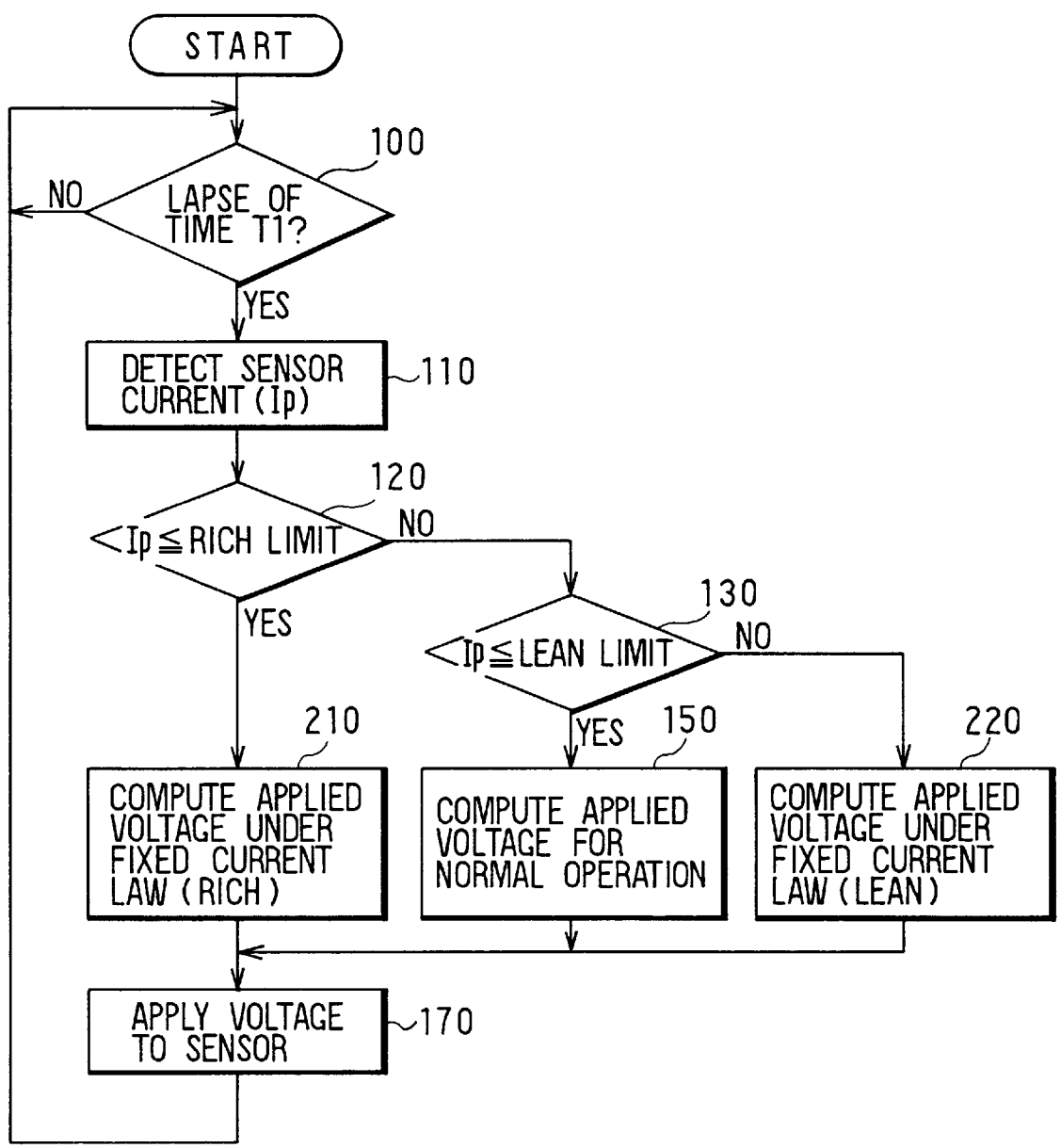
FIG. 12 is a flowchart showing a procedure for detecting a sensor-current and controlling a voltage applied to the A/F sensor according to a second embodiment.

In FIG. 12, the steps 140 and 160 shown in FIG. 6 are replaced by steps 210 and 220 respectively. If the sensor-current Ip is found equal to or smaller than the rich-side limit of the air-fuel ratio detection zone at the step 120 of the flowchart shown in FIG. 12, that is, if the result of the determination made by the microprocessor 20 at the step 120 is YES, the flow of processing proceeds to the step 210 at which the microprocessor 20 computes the magnitude of the applied voltage Vp from the value of the sensor-current Ip detected at the step 110. In the computation, a control constant stored in advance in a ROM unit is used so as to give a value of the applied voltage Vp that brings the sensor-current Ip to a predetermined target value Ip1. That is, the applied voltage Vp is computed by using typically Eq. (1) given as follows.

$$Vp = Va - K \times (Ip - \text{Target } Ip1) \quad (1)$$

where notation Va is a fixed value for controlling the sensor-current to a value in the sensor-current detection zone and notation K is the control constant. The target Ip1 is set in advance as a sensor-current at a value slightly outside the air-fuel ratio detection zone on the richer side. According to Eq.(1), the applied voltage Vp is controlled in accordance with a variation between the measured value Ip of the sensor-current and the target value Ip1. That is, if the value of Ip becomes greater than the target value Ip1, the applied voltage Vp is decreased so as to reduce Ip to Ip1. If the value of Ip becomes smaller than the target value Ip1, on the other hand, the applied voltage Vp is increased so as to raise Ip to Ip1.

If the sensor-current Ip is found greater than the lean-side limit of the air-fuel ratio detection zone at the step 130 of the flowchart shown in FIG. 12, that is, if the result of the determination made by the microprocessor 20 at the step 130 is NO, the flow of processing proceeds to the step 220 at which the microprocessor 20 computes the magnitude of the applied voltage Vp from the value of the sensor-current Ip detected at the step 110. In the computation, the control constant K stored in advance in the ROM unit is used so as to give a value of the applied voltage Vp that brings the sensor-current Ip to a predetermined target value Ip2. That is, the applied voltage Vp is computed by using typically Eq. (2) given as follows.

$$Vp = Vb + K \times (\text{Target } Ip2 - Ip) \quad (2)$$

where, much like Va used in Eq. (1), notation Vb is a fixed value for controlling the sensor-current to a value in the sensor-current detection zone. The target Ip2 is set in advance as a sensor-current at a value slightly outside the air-fuel ratio detection zone on the leaner side. According to Eq.(2), the applied voltage Vp is controlled in accordance with a variation between the measured value Ip of the sensor-current and the target value Ip2. That is, if the value of Ip becomes greater than the target value Ip2, the applied voltage Vp is decreased so as to reduce Ip to Ip2. If the value of Ip becomes smaller than the target value Ip2, on the other hand, the applied voltage Vp is increased so as to raise Ip to Ip2.

It should be noted that, if the results of the determinations made at the steps 120 and 130 indicate that (the rich-side limit<Ip≦the lean-side limit), the flow of processing goes on to the step 150 at which the microcomputer 20 computes the value of the voltage Vp to be applied to the A/F sensor 30 for the sensor-current Ip detected at the step 110 by using the characteristic line L2 of FIG. 7 which is stored in advance in the ROM unit. The voltage Vp to be applied to the A/F sensor 30 is a voltage for use in an operation in a normal state. Thereafter, the flow of processing proceeds from the step 210, 150 or 220 the a step 170 at which the microcomputer 20 makes a bias command signal Vr from the applied voltage Vp computed at the step 210, 150 or 220, outputting the bias command signal Vr to the D/A converter 21. In this way, the desired voltage Vp is applied to the A/F sensor 30.

Figure 13:
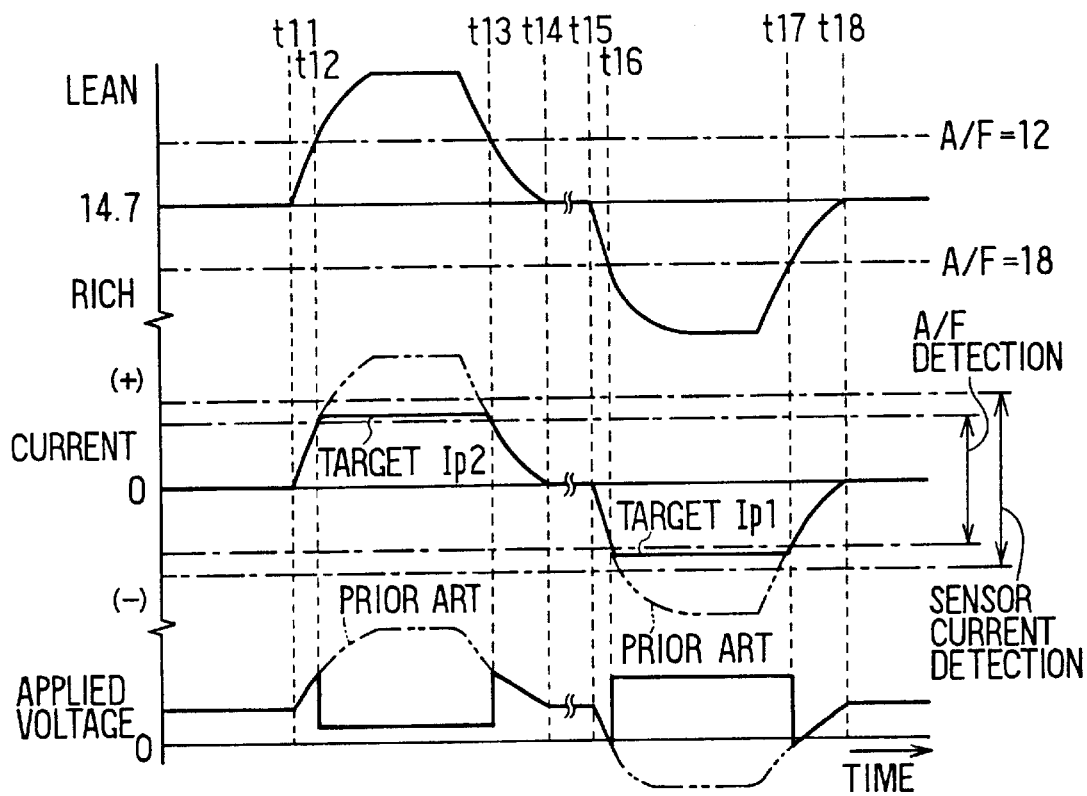
FIG. 13 is a time chart showing the operations of the second embodiment.

Operations carried out in the events of changes in air-fuel ratio caused by a fuel cut-off and an increase in load to a heavy value is shown in FIG. 13. In a period between points of time t11 and t14 shown in FIG. 13, the air-fuel ratio changes to a value in the lean zone in the event of a fuel cut-off. In a period between points of time t15 and t18, on the other hand, the air-fuel ratio changes to a value in the rich zone in the event of injection of a large amount of fuel in response to an increase in load to a heavy one. It should be noted that, in the time chart shown in FIG. 13, solid lines represent the sensor-current and the applied voltage generated in accordance with the control implemented by the present embodiment while double-dotted lines represent the sensor-current and the applied voltage generated in accordance with the conventional control, that is, the control of the applied voltage using the characteristic line Lx shown in FIG. 21.

More specifically, at the point of time t11 where the fuel cut-off is started, the air-fuel ratio changes to a value located far in the lean zone and the sensor-current accordingly changes to a value located far on the positive side. Later on, at a point of time t12 where the sensor-current reaches a value on the lean-side limit of the air-fuel ratio detection zone corresponding to an A/F of 18, the sensor-current is feedback-controlled toward the target Ip2 to bring the applied voltage to a fixed value. That is, prior to the point of time t12, the applied voltage is controlled by using the characteristic line L2 shown in FIG. 7. After the point of time t12, however, the control of the applied voltage is controlled at the fixed value.

At a predetermined time, the injection of fuel by the injector is resumed and the air-fuel ratio starts to drop, being accompanied by a decrease in sensor-current. As the sensor-current decreases to a value smaller than a limit value on the lean side at a point of time t13, the applied voltage is thereafter controlled by again using the characteristic line L2 shown in FIG. 7. Finally, at the point of time t14, the air-fuel ratio is restored to the stoichiometric air-fuel ratio.

Comparison of the control according to the present embodiment with the conventional control during the period where the air-fuel ratio goes beyond the air-fuel ratio detection zone, getting in the lean zone, that is, during the period between the points of time t12 and t13, indicates that, in the case of the conventional control shown by the double-dotted lines, the applied voltage rises following the change in air-fuel ratio, causing the sensor-current to go far beyond the sensor-current detection zone. In the case of the control implemented by the present embodiment shown by the solid lines, on the other hand, it is obvious that the sensor-current is limited to values in the sensor-current detection zone when the air-fuel ratio changes.

On the other hand, when injection of a large amount of fuel in response to an increase in load to a heavy one is started at a point of time t15, after the point of time t15 at which the load starts to increase to a high value, the air-fuel ratio greatly changes to a value in the rich zone and the current also changes to a value on the negative side due to the change in air-fuel ratio. Later on, at a point of time t16 where the sensor-current reaches a value on the rich-side limit of the air-fuel ratio detection zone corresponding to an A/F of 12, the sensor-current is feedback-controlled toward the target Ip1 to bring the applied voltage to a fixed value. That is, prior to the point of time t16, the applied voltage is controlled by using the characteristic line L2 shown in FIG. 7. After the point of time t16, however, the control of the applied voltage is controlled at the fixed value.

Thereafter, when the increase in load to a heavy value disappears, the sensor-current starts to rise due to an increase in air-fuel ratio. As the sensor-current exceeds the rich-side limit at a point of time t17, the applied voltage is thereafter controlled by again using the characteristic line L2 shown in FIG. 7. Finally, at the point of time t18, the air-fuel ratio is restored to the stoichiometric air-fuel ratio.

Comparison of the control according to the present embodiment with the conventional control during the period where the air-fuel ratio goes beyond the air-fuel ratio detection zone, getting in the rich zone, that is, during the period between the points of time t16 and t17, indicates that, in the case of the conventional control shown by the double-dotted lines, the applied voltage decreases following the change in air-fuel ratio, causing the sensor-current to go far beyond the sensor-current detection zone. In the case of the control implemented by the present embodiment shown by the solid lines, on the other hand, it is obvious that the sensor-current is limited to values in the sensor-current detection zone when the air-fuel ratio changes.

Advantages exhibited by the second embodiment are described as follows.

(a) In the present embodiment, in zones outside the air-fuel ratio detection zone, the voltage applied to the A/F sensor 30 is controlled so as to bring the sensor-current to a predetermined target value. By controlling the sensor-current toward the predetermined target value, the sensor-current will neither increase nor decrease unexpectedly. As a result, much like the first embodiment, the sensor-current can be suppressed properly in a zone outside the air-fuel ratio detection zone. In addition, it is also possible to substantially reduce the amount of heat dissipated in the bias control circuit 40.

(b) Since the target values of the sensor-current are set at locations outside the air-fuel ratio detection zone but within the sensor-current detection zone, the sensor-current can be controlled to a value in the sensor-current detection zone with a high degree of reliability.

Figure 14:
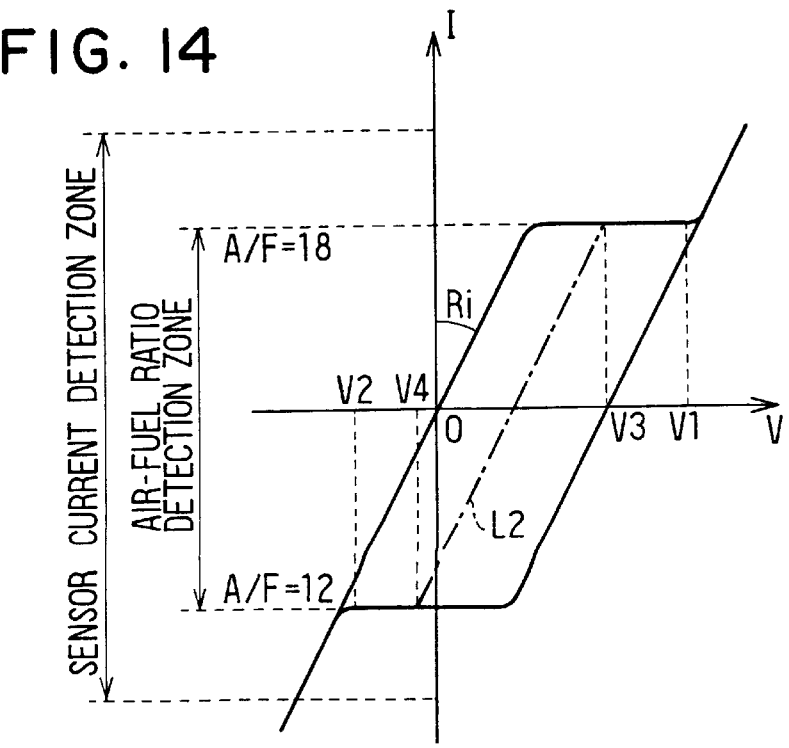
FIG. 14 is a diagram showing a V-I characteristic used for explaining the applied-voltage characteristic of the A/F sensor in the second embodiment.

It should be noted that it is desirable to limit the maximum value of the voltage applied at that time in the lean zone (the zone on upper-limit side) outside the air-fuel ratio detection zone at V1 shown in FIG. 14 and to limit the minimum value of the voltage applied at that time in the rich zone (the zone on lower-limit side) outside the air-fuel ratio detection zone at V2 shown in the figure. V1 and V2 are each a limit value that allows the limit-current detection zone (comprising the straight line segments parallel to the V axis) to be used at any time in the air-fuel ratio detection zone for the A/F sensor 30.

In this case, even if the air-fuel ratio changes, exceeding the upper or lower limit of the air-fuel detection zone, the accuracy of the detection of the sensor-current can be maintained without applying an excessive voltage to the A/F sensor 30, that is, without applying a voltage higher than required on the lean-side limit of the limit-current detection zone or a voltage lower than required on the rich-side limit of the limit-current detection zone of the V-I characteristic shown in FIG. 14 to the sensor 30.

As means for further enhancing the detection accuracy, it is desirable to control the voltage applied to the A/F sensor 30 in the lean zone outside the air-fuel ratio detection zone to a value lower than V3 shown in FIG. 14, the value of the applied voltage on the lean-side limit of the air-fuel ratio detection zone, and to control the voltage applied to the A/F sensor 30 in the rich zone outside the air-fuel ratio detection zone to a value higher than V4 shown in FIG. 14, the value of the applied voltage on the rich-side limit of the air-fuel ratio detection zone.

(Third Embodiment)

In the third embodiment, the control of the applied voltage is started in order to limit the sensor-current only after a predetermined period of time has lapsed since a shift of the sensor-current to a zone outside the air-fuel ratio detection zone.

Figure 15:
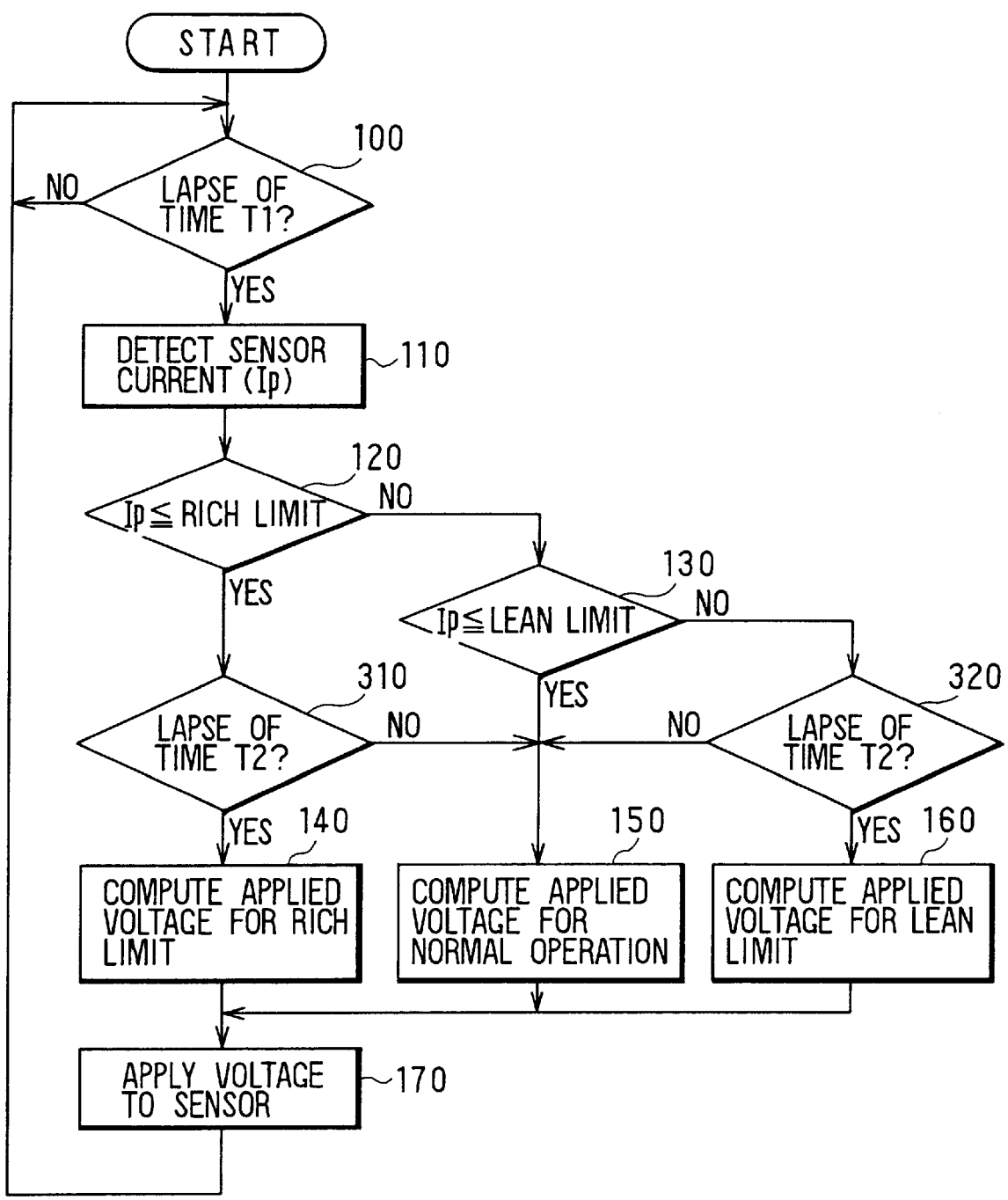
FIG. 15 is a flowchart showing a procedure for detecting a sensor-current and controlling a voltage applied to the A/F sensor according to a third embodiment.
Figure 16:
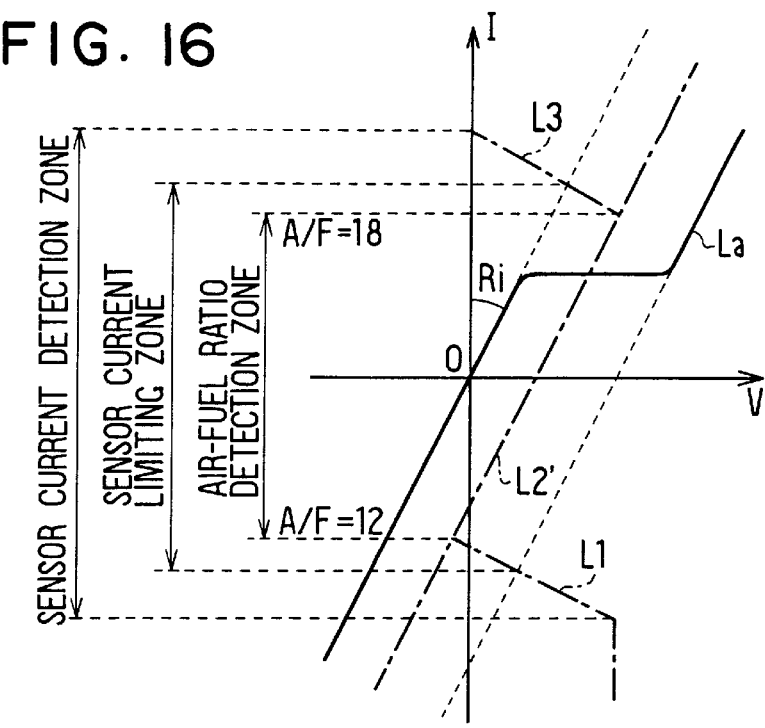
FIG. 16 is a diagram showing a V-I characteristic used for explaining the applied-voltage characteristic of the A/F sensor in the third embodiment.

In this embodiment, as shown in FIG. 15, steps 310 and 320 are added. In the flowchart shown in FIG. 15, if the sensor-current Ip is found equal to or smaller than the rich-side limit of the air-fuel ratio detection zone at the step 120 of the flowchart shown in FIG. 12, that is, if the result of the determination made by the microprocessor 20 at the step 120 is YES, the flow of processing proceeds to a step 310. At the step 310, the microprocessor 20 makes a determination as to whether or not a predetermined time period T2 has lapsed since the YES determination made at the step 120. Even though T2 is set at 2 seconds in the third embodiment, a value in the zone 2 to 5 seconds is considered to be appropriate. If the time period T2 has not lapsed, the flow of operation goes on to the step 150. If the time period T2 has lapsed, on the other hand, the flow of operation goes on to a step 140. That is, even for Ip≦Rich-side limit, the ordinary control of the applied voltage is implemented till the predetermined time period T2 lapses. The control of the applied voltage to limit the sensor-current in the rich zone is not carried out until the predetermined time period T2 has lapsed. In the case of the third embodiment, however, the characteristic line L2 used in the ordinary control of the applied voltage carried out at the step 150 has straight-line extensions in the zones outside the air-fuel ratio detection zone as shown in FIG. 16. The extended characteristic line is denoted by notation L2'. It should be noted that the characteristic lines L1 and L3 are the same as those shown in FIG. 7.

If the sensor-current Ip is found greater than the lean-side limit of the air-fuel ratio detection zone at the step 130 of the flowchart shown in FIG. 12, that is, if the result of the determination made by the microprocessor 20 at the step 130 is NO, the flow of processing proceeds to a step 320. At the step 320, the microprocessor 20 makes a determination as to whether or not the predetermined time period T2 has lapsed since the NO determination made at the step 130. If the time period T2 has not lapsed, the flow of operation goes on to the step 150. If the time period T2 has lapsed, on the other hand, the flow of operation goes on to a step 160. That is, even for Ip>Lean-side limit, the ordinary control of the applied voltage is implemented using the characteristic line L2' shown in FIG. 16 till the predetermined time period T2 lapses. The control of the applied voltage to limit the sensor-current in the lean zone is not carried out until the predetermined time period T2 has lapsed.

Figure 17:
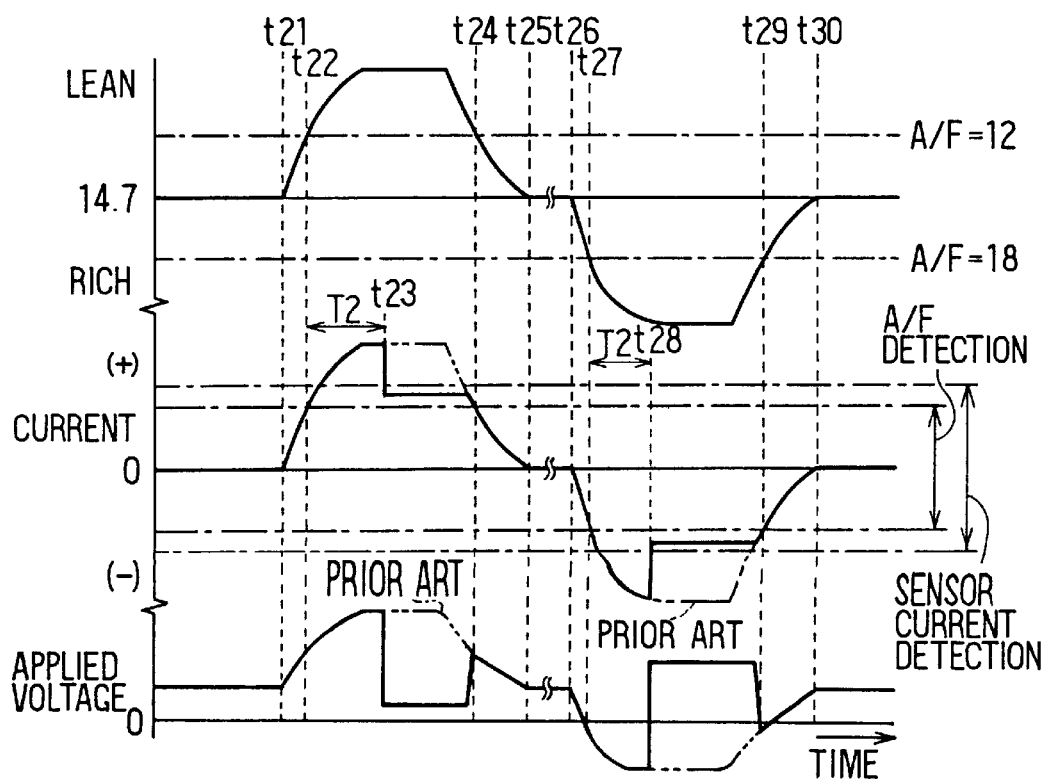
FIG. 17 is a time chart showing the operations of the third embodiment.

As shown in FIG. 17 showing events of changes in air-fuel ratio caused by a fuel cut-off and an increase in load to a heavy value, in a period between points of time t21 and t25, the air-fuel ratio changes to a value in the lean zone in the event of a fuel cut-off. In a period between points of time t26 and t30, on the other hand, the air-fuel ratio changes to a value in the rich zone in the event of injection of a large amount of fuel in response to an increase in load to a heavy one. It should be noted that, in the time chart shown in FIG. 17, solid lines represent the sensor-current and the applied voltage generated in accordance with the control implemented by the present embodiment while double-dotted lines represent the sensor-current and the applied voltage generated in accordance with the conventional control, that is, the control of the applied-voltage using the characteristic line Lx shown in FIG. 21. The following is description in regard to the sequence indicated by the time chart shown in FIG. 17.

First of all, at the point of time t21 where the fuel cut-off is started, the air-fuel ratio changes to a value located far in the lean zone and the sensor-current accordingly changes to a value located far on the positive side. Later on, at a point of time t22, the sensor-current reaches a value on the lean-side limit of the air-fuel ratio detection zone corresponding to an A/F of 18. Thereafter, the sensor-current and the applied voltage both rise, accompanying a continuing increase in air-fuel ratio till the predetermined time period T2 lapses. Then, from a point of time t23 at which the time period T2 lapses since the point of time t22, the applied voltage which has been controlled by using the characteristic line L2' shown in FIG. 16 so far is controlled by using the characteristic line L3 shown in the same figure.

Here, at the point of time t23, a failure diagnosis is carried out to find out whether or not the A/F sensor 30 is functioning normally for the sensor-current flowing at that time.

At a predetermined time, the injection of fuel by the injector is resumed and the air-fuel ratio starts to drop, being accompanied by a decrease in sensor-current. As the sensor-current decreases to a value smaller than a limit value on the lean side at a point of time t24, the applied voltage is thereafter controlled by again using the characteristic line L2' shown in FIG. 16, more specifically, using the portion of the characteristic line L2' in the air-fuel ratio detection zone. Finally, at the point of time t25, the air-fuel ratio is restored to the stoichiometric air-fuel ratio.

As described above, during the period between the points of time t22 and t24, the air-fuel ratio goes beyond the air-fuel ratio detection zone, getting in the lean zone. In particular, during the sub-period between the points of time t22 and t23, the sensor-current once reaches an excessively large value outside the sensor-current detection zone but the length of the sub-period is limited to the predetermined time period T2. As a result, unlike the conventional control shown by the double-dotted line wherein an excessively large sensor-current flows up to a point of time close to t24, the present embodiment is capable of reducing the amount of electric power consumed by the A/F sensor 30.

On the other hand, when injection of a large amount of fuel in response to an increase in load to a heavy one is started at a point of time t26, after the point of time t26 at which the load starts to increase to a high value, the air-fuel ratio greatly changes to a value in the rich zone and the current also changes to a value on the negative side due to the change in air-fuel ratio. Later on, at a point of time t27, the sensor-current reaches a value on the rich-side limit of the air-fuel ratio detection zone corresponding to an A/F of 12. Thereafter, the sensor-current and the applied voltage both decrease, accompanying a continuing decrease in air-fuel ratio till the predetermined time period T2 lapses. Then, from a point of time t28 at which the time period T2 lapses since the point of time t27, the applied voltage which has been controlled by using the characteristic line L2' shown in FIG. 16 so far is controlled by using the characteristic line L1 shown in the same figure.

Thereafter, when the increase in load to a heavy one disappears, the sensor-current starts to rise due to an increase in air-fuel ratio. As the sensor-current exceeds the rich-side limit at a point of time t29, the applied voltage is thereafter controlled by again using the characteristic line L2' shown in FIG. 7, more specifically, using the portion of the characteristic line L2' in the air-fuel ratio detection zone. Finally, at the point of time t30, the air-fuel ratio is restored to the stoichiometric air-fuel ratio.

Much like the control implemented in the event of a fuel cut-off, during the period between the points of time t27 and t29, the air-fuel ratio goes beyond the air-fuel ratio detection zone, getting in the rich zone. In particular, during the sub-period between the points of time t27 and t28, the sensor-current once reaches an excessive value on the negative side outside the sensor-current detection zone but the length of the sub-period is limited to the predetermined time period T2. As a result, unlike the conventional control shown by the double-dotted line wherein an excessive sensor-current flows up to a point of time close to t29, the present embodiment is capable of reducing the amount of electric power consumed by the A/F sensor 30.

Much like the first and second embodiments, according to the third embodiment, the sensor-current can be suppressed properly in a zone outside the air-fuel ratio detection zone. In addition, it is also possible to substantially reduce the amount of heat dissipated in the bias control circuit 40. Furthermore, the third embodiment also exhibits the following advantages as well.

As described above, in the case of the third embodiment, when the air-fuel ratio goes beyond the air-fuel ratio detection zone, the way in which the applied voltage is controlled is kept as it is temporarily and limitation is imposed on the sensor-current later on. As a result, the A/F sensor 30 can be diagnosed for a failure from the state of change in air-fuel ratio occurring in the event of a fuel cut-off or large injection of fuel in response to an increase in load to a heavy value. In this case, even though an excessive sensor-current flows temporarily, an action to limit the sensor-current is taken immediately. As a result, the problems encountered in the conventional control of the applied voltage do not arise.

It should be noted that while the present invention has been described with reference to the first to third embodiments, the description is not to be construed in a limiting sense. That is, the first to third embodiments are no more than preferred embodiments. It is further understood by those skilled in the art that a variety of changes and modifications can thus be made to the embodiments as follows.

Figure 18:
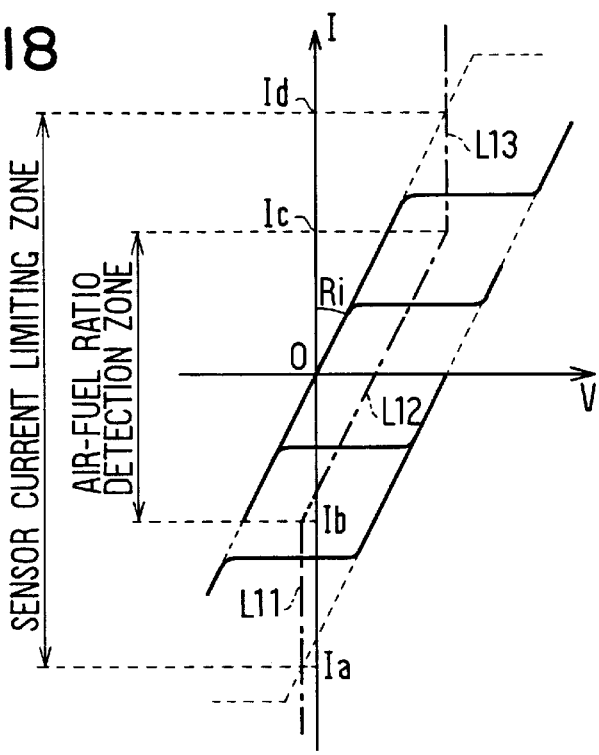
FIG. 18 is a diagram showing a V-I characteristic used for explaining the applied-voltage characteristic of the A/F sensor according to another embodiment.

(1) The characteristic lines can be set as shown in FIG. 18. In the V-I diagram shown in FIG. 18, the characteristic lines for setting the applied voltage are segments L11, L12 and L13. The characteristic line L12 which is identical with L2 shown in FIG. 7 is set in the air-fuel ratio detection zone. The characteristic lines L11 and L13 are straight lines parallel to the I axis set in zones outside the air-fuel ratio detection zone. When the air-fuel ratio goes beyond the air-fuel ratio detection zone, getting in the rich zone, the sensor-current flowing at that time is limited to values in the zone I$a$ to I$b$. When the air-fuel ratio goes beyond the air-fuel ratio detection zone, getting in the lean zone, on the other hand, the sensor-current flowing at that time is limited to values in the zone I$c$ to I$d$. Thus, the sensor-current is limited to values in the zone with a lower limit equal to I$a$ and an upper limit equal to I$d$ no matter how the air-fuel ratio changes. As a result, the object of the invention can be achieved even in such a scheme.

Figure 19:
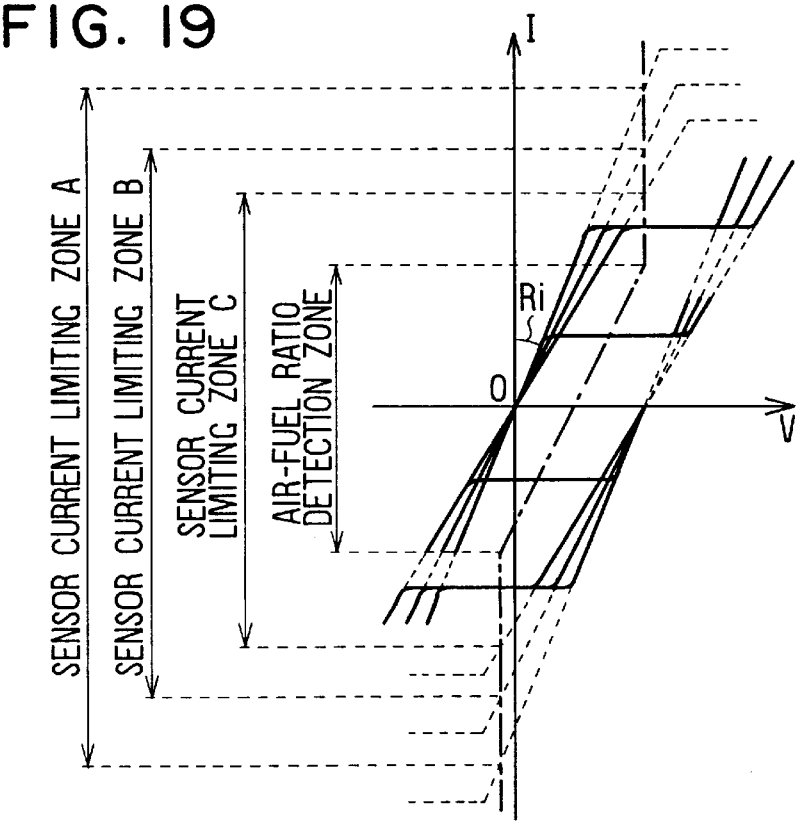
FIG. 19 is a diagram showing a V-I characteristic used for explaining the applied-voltage characteristic of the A/F sensor according to a still another embodiment.

Here, due to changes in element resistance Ri depending upon the activation state of the A/F sensor 30, the sensor-current limitation zone changes to those indicated by notations [A], [B] and [C] as shown in FIG. 19.

(2) The gradients of the characteristic lines L1 and L3 outside the air-fuel ratio detection zone shown in FIG. 7 can be changed or the characteristic lines L1 and L3 can each be set as a multi-stage characteristic line having a plurality of gradients. As an alternative, the characteristic lines L1 and L3 can be combined with the characteristic lines L11 and L13 shown in FIG. 18 respectively to form new characteristic lines. That is, the characteristic lines can be changed into an arbitrary scheme for implementation as long as, in the resulting scheme, the applied voltage is controlled in zones outside the air-fuel ratio detection zone (oxygen-concentration detection zone) by using a characteristic different from the positive characteristic for the air-fuel ratio detection zone (oxygen-concentration detection zone).

Figure 20:
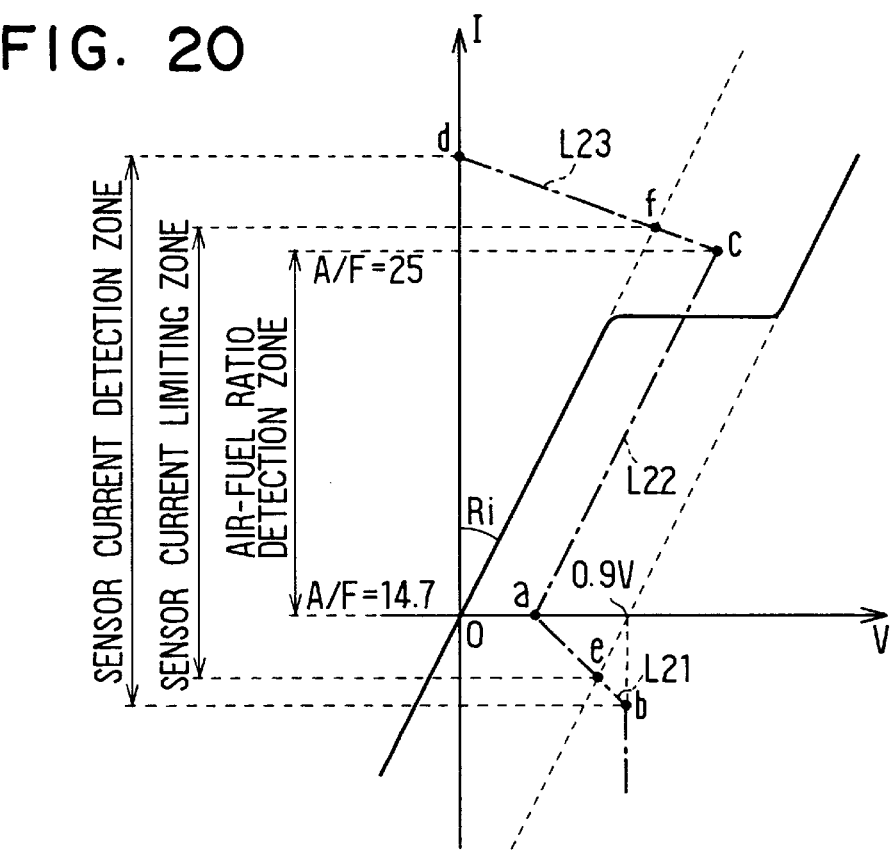
FIG. 20 is a diagram showing a V-I characteristic used for explaining the applied-voltage characteristic of the A/F sensor according to a still further embodiment.

(3) In the embodiments described above, the air-fuel ratio (A/F) detection zone 12 to 18 is set with the stoichiometric air-fuel ratio taken approximately as a center. Of course, the air-fuel ratio detection zone can be changed. FIG. 20 is a V-I characteristic diagram showing an air-fuel ratio detection zone provided in the lean zone. In the V-I characteristic diagram shown in the figure, the air-fuel detection zone covers a zone with an A/F value ranging from 14.7 to 25. In this case, the sensor-current detection zone is also shifted in accordance with the change in air-fuel ratio detection zone. In the example shown in the figure, the sensor-current detection zone is obtained by extending the air-fuel ratio detection zone by an extension of about 20% on each of the lean and rich sides thereof.

In this case, the applied voltage in the air-fuel ratio detection zone is set by using a characteristic line L22 which is the same as the characteristic line L2 shown in FIG. 7. On the other hand, the applied voltage in the rich zone outside the air-fuel ratio detection zone for A/F values smaller than 14.7 is set by using a characteristic line L21 whereas the applied voltage in the lean zone outside the air-fuel ratio detection zone for A/F values greater than 25 is set by using a characteristic line L23. A point a shown in the figure is a rich-side limit of the air-fuel ratio detection zone on the characteristic line L22. On the other hand, a point b is a point of intersection of a limit line of the sensor-current detection zone on the rich side and a line representing an electromotive force of 0.9 V of the A/F sensor 30 on the rich side. The characteristic line L21 includes a linear straight line segment connecting the points a and b. Likewise, a point c shown in the figure is a lean-side limit of the air-fuel ratio detection zone on the characteristic line L22. On the other hand, a point d is a point of intersection of a limit line of the sensor-current detection zone on the lean side and a line representing an electromotive force of 0 V of the A/F sensor 30 on the lean side. The characteristic line L23 includes a linear straight line segment connecting the points c and d.

By setting the characteristic lines L21 and L23 as described above, in a state shown in FIG. 20, that is in a state wherein the element resistance has a predetermined value Ri, it is a matter of course that, for a zone outside the air-fuel ratio detection zone, the sensor-current flowing at that time is limited to values in the sensor-current detection zone, that is, a zone prescribed by the points e and f shown in the figure.

(4) As described earlier, in the second embodiment, the applied voltage Vp is controlled by using a term proportional to a variation between the measured value Ip of the sensor-current and the target value Ip1 or Ip2 in accordance with either of the following equations.

$$Vp=Va-K \times (Ip-\text{Target } Ip1) \quad (1)$$

$$Vp=Vb+K \times (\text{Target } Ip2-Ip) \quad (2)$$

It should be noted, however, that the equations may be changed. For example, the target value of the sensor-current can be a variable depending on, among other conditions, the operating state of the engine. As an alternative, the applied voltage Vp can be controlled by using an integral and/or differential term.

(5) As described earlier, the flowchart of the third embodiment shown in FIG. 15 is obtained by adding the steps 310 and 320 to the flowchart of the first embodiment shown in FIG. 6. It should be noted that the steps 310 and 320 can also be added to the flowchart of the second embodiment shown in FIG. 12.

(6) In the case of the third embodiment, for a sensor-current outside the air-fuel ratio detection zone, the characteristic line L2' shown in FIG. 16, more specifically, an extension of the characteristic line L2' outside the air-fuel ratio detection zone is used for temporarily controlling the applied voltage in place of the control to limit the sensor-current. In this case, the characteristic lines L11 and L13 shown in FIG. 18 can be used instead of the characteristic line L2' shown in FIG. 16

(7) When the air-fuel ratio (the sensor-current) goes beyond the air-fuel ratio detection zone, the ordinary control of the applied voltage can be continued as it is temporarily as is the case with the third embodiment. Instead of temporarily continuing the ordinary control each time the air-fuel ratio goes beyond the air-fuel ratio detection zone, such temporary ordinary control can be continued periodically for each number of times the air-fuel ratio goes beyond the air-fuel ratio detection zone. For example, the number of times the air-fuel ratio goes beyond the air-fuel ratio detection zone is counted and only when the count exceeds a predetermined value typically in the zone 10 to 20, is the ordinary control continued temporarily. As an alternative, the ordinary control is continued temporarily only when the air-fuel ratio goes beyond the air-fuel ratio detection zone for the first time since the start of the engine.

As another alternative, the ordinary control is continued temporarily only when the air-fuel ratio gets in the lean zone and not when the air-fuel ratio gets in the rich zone. As still another alternative, the ordinary control is continued temporarily only when the air-fuel ratio gets in the rich zone and not when the air-fuel ratio gets in the lean zone. In this case, the step 310 or 320 is deleted from the flowchart shown in FIG. 15.

(8) In the embodiments described above, the present invention is implemented by using a cup-shaped A/F sensor (an air-fuel ratio sensor of a limit-current type). It should be noted that the present invention can also be implemented by using an A/F sensor of a plate-layer type. In this case, the zone for outputting a pumping current of the stacked-plate A/F sensor needs to be controlled properly.

(9) The oxygen sensor provided by the present invention can be used in applications where the oxygen sensor serves as an air-fuel ratio sensor. That is, the oxygen sensor can be used in any application as long as the objective of the application is to detect the concentration of oxygen.

The present invention may be further modified or altered without departing from the spirit of the invention.

We claim:

1. An oxygen-concentration detecting apparatus comprising:

an oxygen sensor for outputting a current signal representing a concentration of oxygen contained in gas when a voltage is applied to said oxygen sensor; and voltage control means for controlling said voltage applied to said oxygen sensor so as to limit said current signal flowing through said oxygen sensor to a predetermined value in a zone outside a predetermined range of oxygen-concentrations defining an oxygen-concentration detection zone, wherein said voltage control means is constructed to change said voltage gradually toward a minimum value of an electromotive force of said oxygen sensor when said current signal flowing through said oxygen sensor is in a zone outside said oxygen-concentration detection zone on an upper-limit side, and toward a maximum value of said electromotive force of said oxygen sensor when said current signal flowing through said oxygen sensor in a zone outside said oxygen-concentration detection zone on a lower-limit side.

2. An oxygen-concentration detecting apparatus according to claim 1, wherein detection of said oxygen-concentration is continued temporarily and later on said voltage applied to said oxygen sensor is controlled in order to impose a limit on said current flowing through said oxygen sensor, when said current signal flowing through said oxygen sensor goes beyond said oxygen-concentration detection zone.

3. An oxygen-concentration detecting apparatus comprising:

an oxygen sensor for outputting a current signal representing a concentration of oxygen contained in gas when a voltage is applied to said oxygen sensor; and voltage control means for controlling said voltage applied to said oxygen sensor in dependence on said current signal flowing through said oxygen sensor according to a voltage-current characteristic having a positive gradient defining a predetermined positive characteristic in a voltage-current relation in a predetermined range of oxygen-concentrations defining an oxygen-concentration detection zone, and according to a characteristic different from said positive characteristic in a zone outside said predetermined oxygen-concentration detection zone, wherein said voltage control means is constructed to change said voltage gradually toward a minimum value of an electromotive force of said oxygen sensor when said current signal flowing through said oxygen sensor is in a zone outside said oxygen-concentration detection zone on an upper-limit side, and toward a maximum value of said electromotive force of said oxygen sensor when said current signal flowing through said oxygen sensor in a zone outside said oxygen-concentration detection zone on a lower-limit side.

4. An oxygen detecting apparatus according to claim 3, wherein said voltage control means is constructed to control said voltage according to an applied-voltage characteristic line set for said oxygen sensor so as to limit said current flowing though said oxygen sensor in a zone outside said oxygen-concentration detection zone but within a range of sensor currents defining a sensor-current detection zone which is wider than said oxygen-concentration detection zone by a predetermined width.

5. An oxygen-concentration detecting apparatus according to claim 4, wherein said voltage control means is constructed to control said voltage by using said applied-voltage characteristic line connecting a point at an upper end of said applied-voltage characteristic line inside said oxygen-concentration detection zone to a point of intersection of an upper limit line of said sensor-current detection zone and a line representing said minimum value of said electromotive force of said oxygen sensor when said current signal flowing through said oxygen sensor in said sensor-current detection zone outside said oxygen-concentration detection zone on said upper-limit side, and by using said applied-voltage characteristic line connecting a point at a lower end of said applied-voltage characteristic line inside said oxygen-concentration detection zone to a point of intersection of a lower limit line of said sensor-current detection zone and a line representing said maximum value of said electromotive force of said oxygen sensor when said current signal flowing through said oxygen sensor is in said sensor-current detection zone outside said oxygen-concentration detection zone on a lower limit side.

6. An oxygen-concentration detecting apparatus comprising:

an oxygen sensor for outputting a current signal representing a concentration of oxygen contained in a gas when a voltage is applied to said oxygen sensor; and voltage control means for feedback-controlling said voltage applied to said oxygen sensor to cause said current signal flowing through said oxygen sensor to a target value in a zone outside a predetermined range of oxygen-concentrations defining an oxygen-concentration detection zone, wherein said voltage control means is constructed to limit a maximum value of said voltage applied to said oxygen sensor when said current signal flowing through said oxygen sensor is in a zone outside said oxygen-concentration detection zone on an upper-limit side, and to limit a minimum value of said voltage applied to said oxygen sensor when said current flowing through said oxygen sensor is in a zone outside said oxygen-concentration detection zone on a lower-limit side.

7. An oxygen-concentration detecting apparatus according to claim 6, wherein said target value is set at a value outside said oxygen-concentration detection zone but within a sensor-current detection zone wider than said oxygen-concentration detection zone by a predetermined width.

8. An oxygen-concentration detecting apparatus according to claim 6, wherein said voltage control means is constructed to control said voltage applied to said oxygen sensor to a level lower than an applied-voltage value corresponding to the upper end of an applied-voltage characteristic line inside said oxygen-concentration detection zone when said current signal flowing through said oxygen sensor is in a zone outside said oxygen-concentration detection zone on an upper-limit side, and to a level higher than an applied-voltage value corresponding to the lower end of said applied-voltage characteristic line inside said oxygen-concentration detection zone when said current signal flowing through said oxygen sensor is in a zone outside said oxygen-concentration detection zone on a lower-limit side.

9. An oxygen-concentration detecting apparatus comprising:

an oxygen sensor for outputting a current signal representing a concentration of oxygen contained in gas when a voltage is applied to said oxygen sensor; and voltage control means for controlling said voltage applied to said oxygen sensor so as to limit said current signal flowing through said oxygen sensor to a predetermined value in a zone outside a predetermined range of oxygen-concentrations defining an oxygen-concentration detection zone, wherein said voltage control means is constructed to attain at least one of:

when said current signal flowing through said oxygen sensor is on an upper-limit side outside said predetermined oxygen-concentration detection zone, to change said voltage to a value smaller than a value applied at the time of an upper limit value of said current signal flowing in said predetermined oxygen-concentration detection zone so that said current signal is increased to a value larger than said upper limit value flowing in said predetermined oxygen-concentration detection zone; and when said current signal flowing through said oxygen sensor is on a lower-limit side outside said predetermined oxygen-concentration detection zone, to change said voltage to a value larger than a value applied at the time of a lower limit value of said current signal flowing in said predetermined oxygen-concentration detection zone so that said current signal is decreased to a value lower than said lower limit value flowing in said predetermined oxygen-concentration detection zone.

10. An oxygen-concentration detecting apparatus comprising:

an oxygen sensor for outputting a current signal representing a concentration of oxygen contained in gas when a voltage is applied to said oxygen sensor; and voltage controller controlling said voltage applied to said oxygen sensor so as to limit said current signal flowing through said oxygen sensor to a predetermined value in a zone outside a predetermined range of oxygen-concentrations defining an oxygen-concentration detection zone, wherein said voltage controller is arranged to change said voltage gradually toward a minimum value of an electromotive force of said oxygen sensor when said current signal flowing through said oxygen sensor is in a zone outside said oxygen-concentration detection zone on an upper-limit side, and toward a maximum value of said electromotive force of said oxygen sensor when said current signal flowing through said oxygen sensor in a zone outside said oxygen-concentration detection zone on a lower-limit side.

11. An oxygen-concentration detecting apparatus according to claim 10, wherein said voltage controller comprises a programmed microcomputer.

12. An oxygen-concentration detecting apparatus comprising:

an oxygen sensor for outputting a current signal representing a concentration of oxygen contained in gas when a voltage is applied to said oxygen sensor; and voltage controller controlling said voltage applied to said oxygen sensor in dependence on said current signal flowing through said oxygen sensor according to a voltage-current characteristic having a positive gradient defining a predetermined positive characteristic in a voltage-current relation in a predetermined range of oxygen-concentrations defining an oxygen-concentration detection zone, and according to a characteristic different from said positive characteristic in a zone outside said predetermined oxygen-concentration detection zone, wherein said voltage controller is arranged to change said voltage gradually toward a minimum value of an electromotive force of said oxygen sensor when said current signal flowing through said oxygen sensor is in a zone outside said oxygen-concentration detection zone on an upper-limit side, and toward a maximum value of said electromotive force of said oxygen sensor when said current signal flowing through said oxygen sensor in a zone outside said oxygen-concentration detection zone on a lower-limit side.

13. An oxygen-concentration detecting apparatus according to claim 12, wherein said voltage controller is a programmed microcomputer.

14. An oxygen-concentration detecting apparatus comprising:

an oxygen sensor for outputting a current signal representing a concentration of oxygen contained in a gas when a voltage is applied to said oxygen sensor; and voltage controller feedback-controlling said voltage applied to said oxygen sensor to cause said current signal flowing through said oxygen sensor to a target value in a zone outside a predetermined range of oxygen-concentrations defining an oxygen-concentration detection zone, wherein said voltage controller is arranged to limit a maximum value of said voltage applied to said oxygen sensor when said current signal flowing through said oxygen sensor is in a zone outside said oxygen-concentration detection zone on an upper-limit side, and to limit a minimum value of said voltage applied to said oxygen sensor when said current flowing through said oxygen sensor is in a zone outside said oxygen-concentration detection zone on a lower-limit side.

15. An oxygen-concentration detecting apparatus according to claim 14, wherein said voltage controller is a programmed microcomputer.

* * * * *